US012690753B2

(12) United States Patent
Leong et al.

(10) Patent No.: US 12,690,753 B2
(45) Date of Patent: *Jul. 28, 2026

(54) VIDEO ENDOSCOPE WITH FLEXIBLE TIP

(71) Applicant: Verathon Inc., Bothell, WA (US)

(72) Inventors: Gary Leong, New Westminster (CA); Reza Yazdi, Coquitlam (CA); Matthew Pryl, North Vancouver (CA); Bernard Lambrechts, Burnaby (CA); Rohan Sidhu, Abbotsford (CA); Yongkook Kim, Port Moody (CA)

(73) Assignee: Verathon Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,077

(22) Filed: Sep. 28, 2023

(65) Prior Publication Data

US 2024/0023793 A1     Jan. 25, 2024

Related U.S. Application Data

(63) Continuation of application No. 16/415,145, filed on May 17, 2019, now Pat. No. 11,800,971.

(Continued)

(51) Int. Cl.
*A61B 1/005*        (2006.01)
*A61B 1/00*         (2006.01)

(52) U.S. Cl.
CPC ........ *A61B 1/0052* (2013.01); *A61B 1/00066* (2013.01); *A61B 1/0057* (2013.01); *A61B 1/005* (2013.01)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 5,199,950 A * 4/1993 Schmitt ............. A61M 25/0147
                                                604/95.04
5,431,150 A * 7/1995 Yabe ...................... A61B 46/10
                                                600/157

(Continued)

FOREIGN PATENT DOCUMENTS

EP              3 047 786 A1     7/2016

*Primary Examiner* — Ryan N Henderson
(74) *Attorney, Agent, or Firm* — Duane Morris LLP

(57)          ABSTRACT

An endoscope device comprises a handle, a shaft projecting from the handle, wherein the shaft includes a proximal portion and a distal portion relative to the handle, a flexible tip coupled to the distal portion of the shaft, a pair of pull wires extending from the handle portion through the shaft portion and coupled to the flexible tip, a control wheel assembly rotationally secured within the handle and operatively coupled to the pair of pull wires, and a control lever coupled to the control wheel assembly via an opening in the handle. Manipulation of the control lever causes rotation of the control wheel assembly, which then causes deflection of the flexible tip via the pull wires. The control wheel assembly includes an arcuate member that covers at least a portion of the control wheel assembly to prevent external contaminants from entering the opening in the handle adjacent the control lever.

18 Claims, 18 Drawing Sheets

Related U.S. Application Data

(60) Provisional application No. 62/673,268, filed on May 18, 2018.

(58) Field of Classification Search
CPC ... A61B 1/0056; A61B 1/0057; A61B 1/0058; A61B 2017/003; A61B 2017/00318; A61B 2017/00323; A61B 2017/00327; A61M 25/0133; A61M 25/0147; A61M 2025/015
See application file for complete search history.

(56) References Cited

U.S. PATENT DOCUMENTS

| | | | | | |
|---|---|---|---|---|---|
| 5,554,098 | A * | 9/1996 | Yabe | A61B 1/018 | 600/122 |
| 6,852,078 | B2 * | 2/2005 | Ouchi | A61B 1/018 | 600/128 |
| 8,790,250 | B2 * | 7/2014 | Petersen | A61B 1/00066 | 600/149 |
| 8,992,470 | B2 * | 3/2015 | Barenboym | A61M 25/0147 | 604/95.04 |
| 9,968,241 | B2 * | 5/2018 | Iuel | A61B 1/0051 | |
| 10,625,053 | B2 * | 4/2020 | Wang | A61M 25/0136 | |
| 10,959,868 | B2 * | 3/2021 | Cummins | A61F 2/966 | |
| 11,800,971 | B2 * | 10/2023 | Leong | A61B 1/00098 | |
| 2004/0193014 | A1 * | 9/2004 | Miyagi | A61B 1/00042 | 600/118 |
| 2004/0267093 | A1 * | 12/2004 | Miyagi | A61B 1/0052 | 600/152 |
| 2005/0049459 | A1 * | 3/2005 | Hern | A61B 1/00094 | 600/121 |
| 2007/0282167 | A1 * | 12/2007 | Barenboym | A61B 1/0052 | 600/131 |
| 2008/0249362 | A1 * | 10/2008 | Jiang | A61B 1/00137 | 600/121 |
| 2010/0004591 | A1 * | 1/2010 | Barenboym | A61B 1/00042 | 604/95.04 |
| 2010/0217082 | A1 * | 8/2010 | Ito | G02B 23/2476 | 600/121 |
| 2010/0312055 | A1 * | 12/2010 | Konstorum | A61B 1/00066 | 600/131 |
| 2011/0295068 | A1 * | 12/2011 | Petersen | A61B 1/05 | 600/131 |
| 2013/0038930 | A1 * | 2/2013 | Vent | G02B 23/2476 | 359/362 |
| 2013/0085492 | A1 * | 4/2013 | Plascencia, Jr. | A61B 18/1492 | 606/41 |
| 2013/0267778 | A1 * | 10/2013 | Rehe | A61B 1/00096 | 600/125 |
| 2014/0088355 | A1 * | 3/2014 | Schaeffer | A61B 1/233 | 604/528 |
| 2014/0200560 | A1 * | 7/2014 | Lavender | A61B 18/1492 | 606/1 |
| 2015/0359416 | A1 * | 12/2015 | Simchony | A61B 1/0055 | 600/110 |
| 2015/0366436 | A1 * | 12/2015 | Iuel | A61M 25/0147 | 600/149 |
| 2016/0073861 | A1 * | 3/2016 | Kaneko | G02B 23/2476 | 600/125 |
| 2016/0166129 | A1 * | 6/2016 | Walish | A61B 1/307 | 600/104 |
| 2017/0035993 | A1 * | 2/2017 | Quinn | A61B 17/00234 | |
| 2017/0238787 | A1 * | 8/2017 | Hijihara | A61B 1/0052 | |
| 2017/0291008 | A1 * | 10/2017 | Hillukka | A61M 25/0074 | |
| 2018/0028785 | A1 * | 2/2018 | Simmons | A61M 25/09033 | |
| 2018/0303315 | A1 * | 10/2018 | Matthison-Hansen | A61B 17/29 | |
| 2018/0353311 | A1 * | 12/2018 | Cummins | A61M 25/0136 | |
| 2019/0125469 | A1 * | 5/2019 | Yang | A61B 1/00042 | |
| 2020/0229684 | A1 * | 7/2020 | Lund | A61B 1/0052 | |
| 2021/0137355 | A1 * | 5/2021 | Lund | A61B 1/0011 | |
| 2022/0079417 | A1 * | 3/2022 | Rask | A61B 1/00048 | |
| 2022/0280024 | A1 * | 9/2022 | Mo | A61B 1/00066 | |
| 2023/0108741 | A1 * | 4/2023 | Kawakami | A61B 1/0057 | 600/146 |

* cited by examiner

IDENTIFICATION AND AUTHENTICATION LOGIC 1005

VERSION CHECKING LOGIC 1010

SETTINGS STORAGE 1015

DATA LOGGER 1020

LIGHT SOURCE LOGIC 1025

IMAGE CAPTURE LOGIC 1030

IMAGE OUTPUT LOGIC 1035

102

VIDEO ENDOSCOPE WITH FLEXIBLE TIP

CROSS-REFERENCE TO RELATED APPLICATIONS

The present application is a Continuation of U.S. patent application Ser. No. 16/415,145, filed May 17, 2019, which claims priority to U.S. Provisional Patent Application No. 62/673,268, filed May 18, 2018. The entirety of each priority application is hereby incorporated by reference herein.

BACKGROUND

An endoscope refers to a medical device that allows remote examination of the interior of a patient's body. Endoscopes may be used for a variety of diagnostic and treatment procedures relating, for example, to the gastrointestinal and respiratory systems. To increase the ability to view particular internal structures, endoscopes having articulated tips have been designed. However, such articulated endoscopes suffer from problems relating to precision and image quality.

DETAILED DESCRIPTION OF THE PREFERRED EMBODIMENTS

Figure 1:
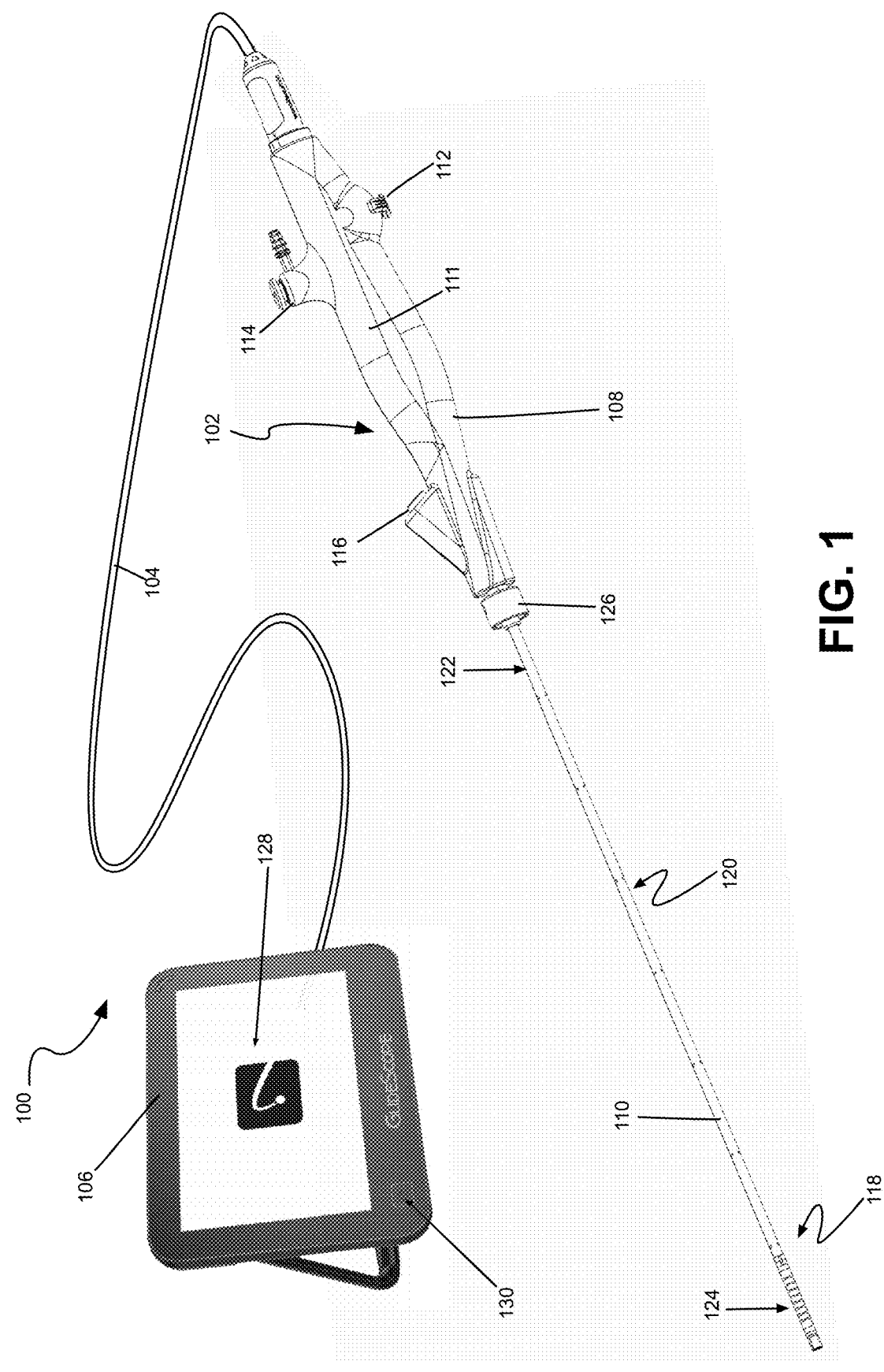
FIG. 1 is a diagram illustrating an endoscope system consistent with embodiments described herein.

The following detailed description refers to the accompanying drawings. The same reference numbers in different drawings may identify the same or similar elements. Also, the following detailed description does not limit the invention.

A video-based endoscope and system are described that allow for examination of a patient's airway to facilitate placement of endotracheal devices (e.g., an endotracheal tube, etc.), delivery of medicine, etc. The system employs video endoscope embodiments that include a flexible tip that is controlled by manipulating a control lever in a handle of the endoscope device. Consistent with implementations described herein, the video endoscope includes a number of components for ensuring accurate and reproducible positioning of the flexible tip. The endoscope further includes a mechanism for engaging the outside diameter on the proximal side of an endotracheal tube concentrically positioned about the endoscope shaft at an initial position proximate the endoscope handle. The endotracheal tube may then be deployed into the patient's airway following the endoscope shaft following accurate placement of the endoscope.

The tip further includes video capture components that capture video and/or images and transmit the video to a remote video monitoring viewable by the user. In addition, the described video endoscope further includes a working channel that facilitates application of negative pressure (suction) and/or delivery of fluid and/or other devices into the airway.

Embodiments of the endoscope described herein include both single-use (i.e., disposable) and reusable endoscopes that include image capturing and lighting elements. During and after insertion of the endoscope into the patient's airway, images obtained from the image capturing elements are conveyed to a video monitor viewable by the endoscope user via a data cable.

Consistent with embodiments described herein, the endoscope, the data cable, and the remote video monitor may each include logic components configured to enable image data to be exchanged between the image capturing element and the video monitor in an efficient and optimized manner.

In exemplary embodiments, the endoscope may include logical components for authenticating the endoscope with other components in the system (e.g., the video monitor and/or data cable) and logging use of the endoscope (e.g., number of times used, dates/times, etc), and for negotiating between components in the endoscope system (e.g., between the endoscope and the video monitor) to determine which component has the most up-to-date software, which may include optimized camera settings and other instructions relevant to the particular endoscope (e.g., based on size, capabilities, age, etc.).

In one exemplary embodiment relating to single-use endoscopes, one or more components of the image capturing element may be included within the data cable, thus rendering the remaining image capturing components in the endoscope less expensive, which is particularly advantageous for a single use device. In such an embodiment, the data cable may include one or more logical components configured to identify when an endoscope has been connected, which endoscope type/size has been connected, and to negotiate with the endoscope and the video monitor to determine which component has a most up-to-date software, which may include optimized camera settings and other instructions relevant to the identified endoscope.

In other embodiments, such as reusable endoscopes, one or more of the logical components of the data cable described above may be integrated within the endoscope and negotiation/communication may take place directly between the endoscope and the video monitor.

Figure 2A:
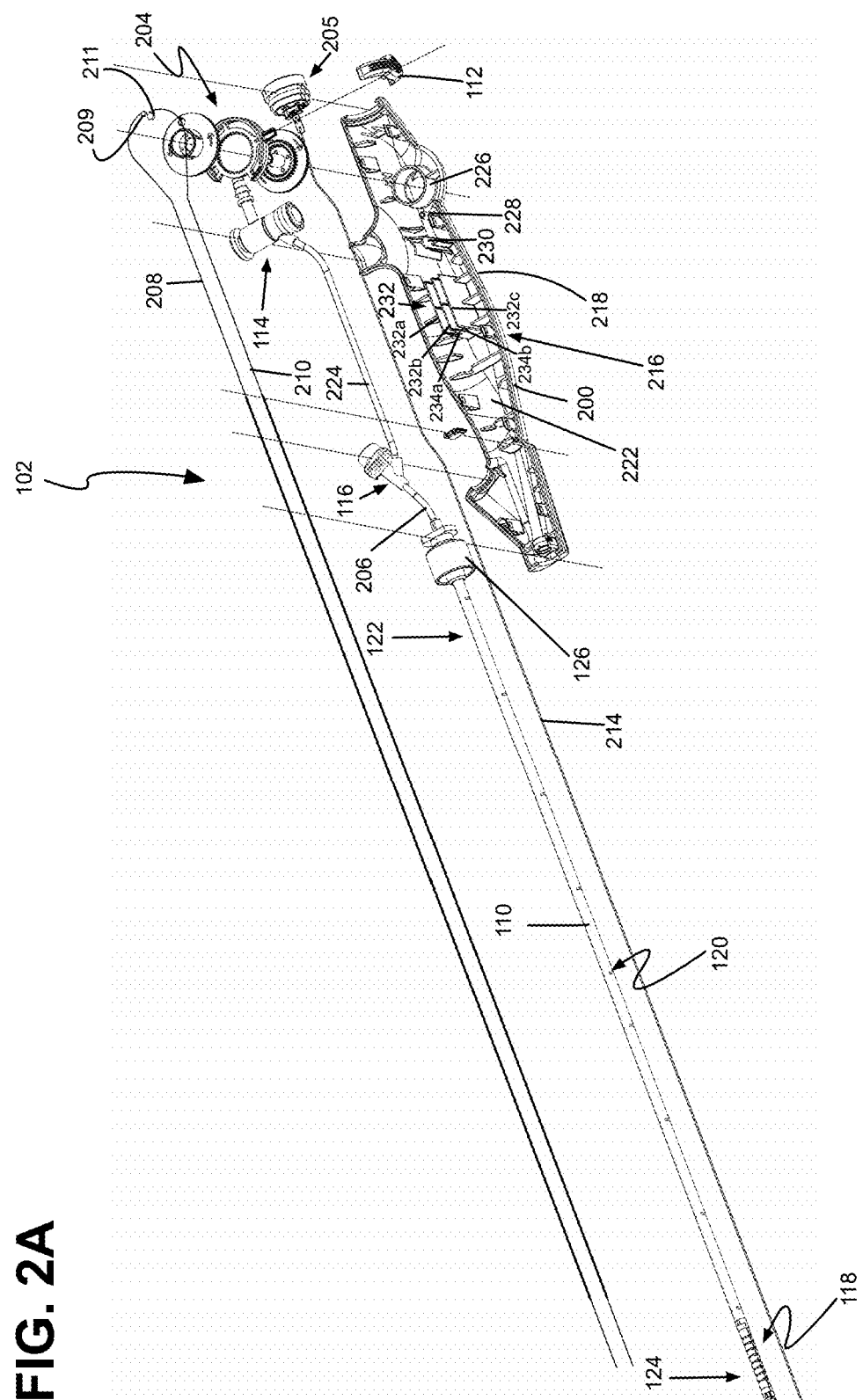
FIG. 2A is an exploded front perspective view of a single-use endoscope configured in accordance with embodiments described herein.
Figure 2B:
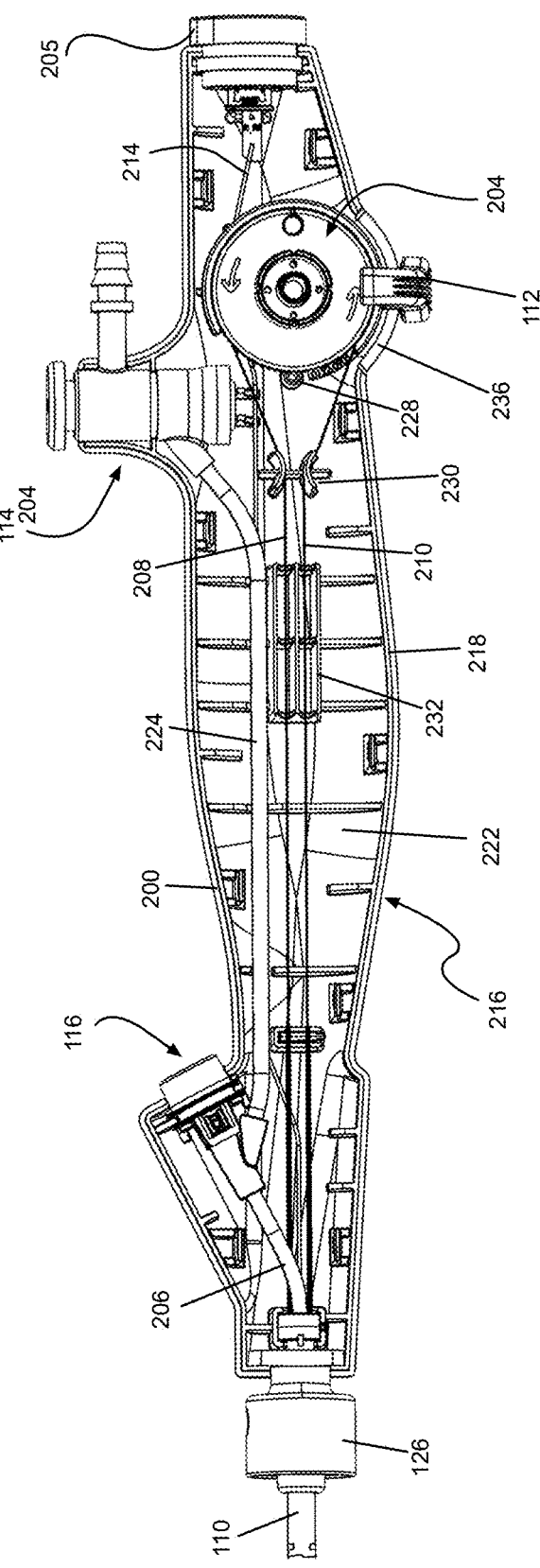
FIG. 2B is a longitudinal cross-sectional view of a handle portion of the endoscope of FIG. 2A.
Figure 2C:
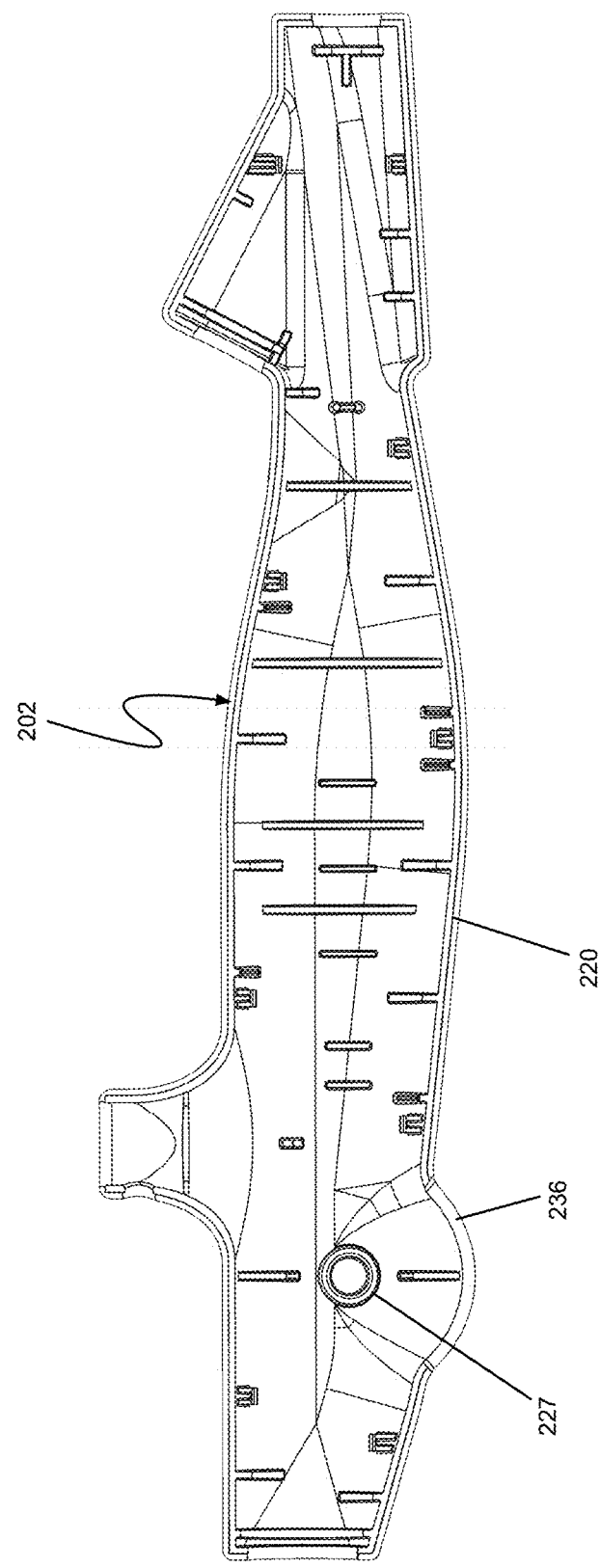
FIG. 2C is a longitudinal cross-sectional view of the handle portion of the endoscope of FIG. 2A illustrating an opposite view than that shown in FIG. 2B.

FIG. 1 illustrates a video endoscope system 100 consistent with implementations described herein. As shown, video endoscope system 100 comprises an endoscope 102, a data cable 104, and a video monitor 106. FIG. 2A is an exploded front perspective view of a single-use endoscope 102 configured in accordance with embodiments described herein. FIG. 2B is a longitudinal cross-sectional view of a handle portion of single-use endoscope 102. FIG. 2C is a longitudinal cross-sectional view of the handle portion illustrating an opposite view than that shown in FIG. 2B.

As shown in FIG. 1, endoscope 102 includes a handle 108 and a shaft 110. Shaft 110 couples with and projects longitudinally from handle 108. As described in additional detail below, handle 108 may be formed of two similarly sized halves, referred to as a right shell 200 (interior features of which are shown in FIG. 2B) and a left shell 202 ((interior features of which are shown in FIG. 2C), which snap or otherwise connect together along a longitudinal center line of handle 108, as shown in FIG. 2A. When assembled, handle 108 includes, among other things, a grip portion 111, a control lever 112, a suction valve assembly 114, an access port assembly 116, control wheel assembly 204, and a data interface assembly 205. Shaft 110 includes a distal end 118, an intermediate portion 120, and a proximal end 122 relative to handle portion 108. Distal end 118 includes a flexible tip 124 and proximal end 122 includes a tube engagement portion 126. Consistent with implementations described herein, dimensions of shaft 110 (e.g., length, outside diameter, and inside diameter) may vary based on an intended use of endoscope 102, such as intended procedures, patient size, etc.

During use, flexible tip 124 of endoscope 102 is introduced into the body cavity being inspected (such as the patient's mouth). A camera module and light source module (described below) are provided at distal end 118 of shaft 110 so as to capture and transmit images of the distal end 118 and corresponding patient anatomy to video monitor 106 via data cable 104.

As described briefly above, in some embodiments data cable 104 may include one or more components of the image capturing element, such as a serializer component. In such an embodiment, the data cable 104 may further include one or more logical components configured to identify when an endoscope has been connected, which endoscope has been connected, and to negotiate with video monitor 106 to determine which of the data cable 104 and the video monitor 106 have the most up-to-date camera settings for use during image capture. In such a single-use embodiment, the combination of the data cable 104 and the endoscope 102 may together perform functions corresponding to a reusable endoscope.

Video monitor 106 may provide power to and initiate image capture from endoscope 102 via data cable 104. For example, as shown in FIG. 1, video monitor 106 may include a display 128, and a control pad 130. Practitioners (e.g., medical personnel) may interface with video monitor 106 during use to initiate image capture, freeze a particular frame, or adjust certain limited settings. Although not shown in the Figures, video monitor 106 may also include a data cable interface for receiving an end of data cable 104, a battery or other power source, and a remote monitor interface for enabling the view of display 128 to be transmitted to one or more other display monitors.

Consistent with embodiments described herein, shaft 110 may be formed of a number of discrete components. In particular, proximal and intermediate portions 122/120 of shaft 110 may be formed of a braided, semi-rigid polymer material having a single lumen therethrough, sized to accommodate the internal components described below. Flexible tip 124, in contrast, may be formed of an extruded polymer material profile formed to include three distinct lumens and cut to provide single-plane flexibility.

Figure 3B:
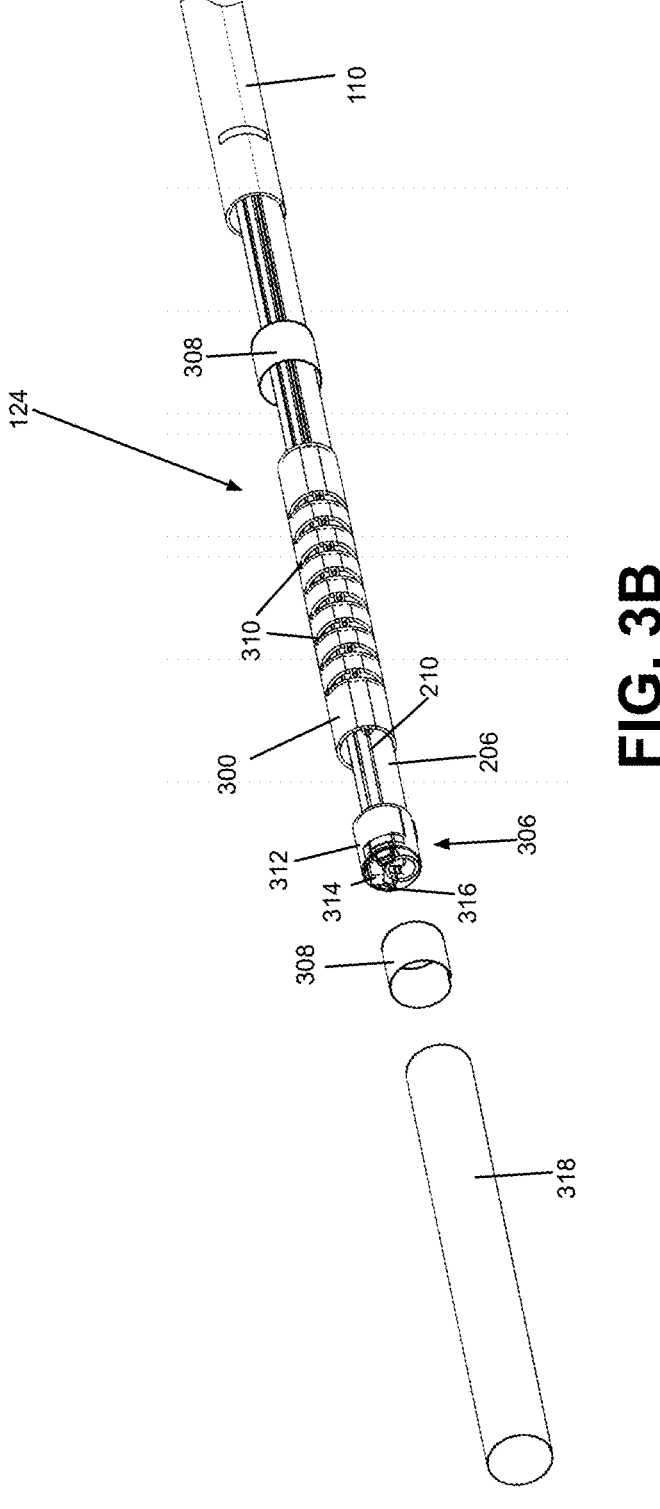
FIGS. 3B and 3C are isometric views of distal end of the endoscope shaft of FIG. 1 in partially assembled and assembled configurations, respectively.
Figure 3C:
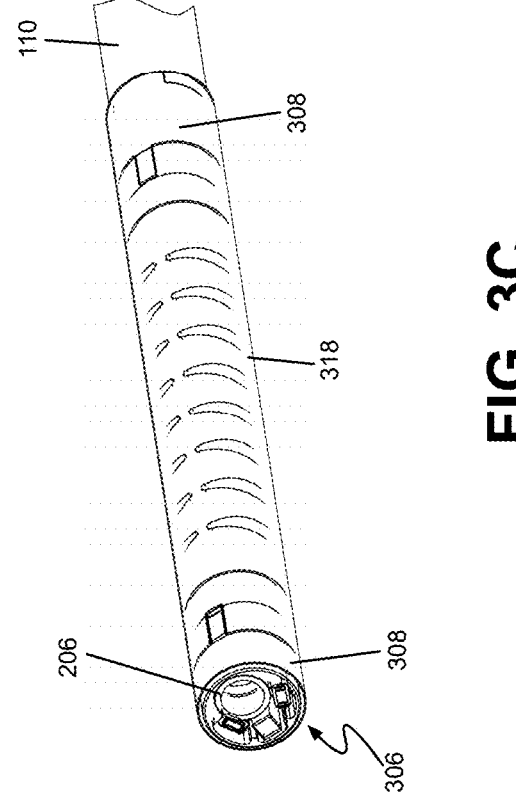
Figure 3A:
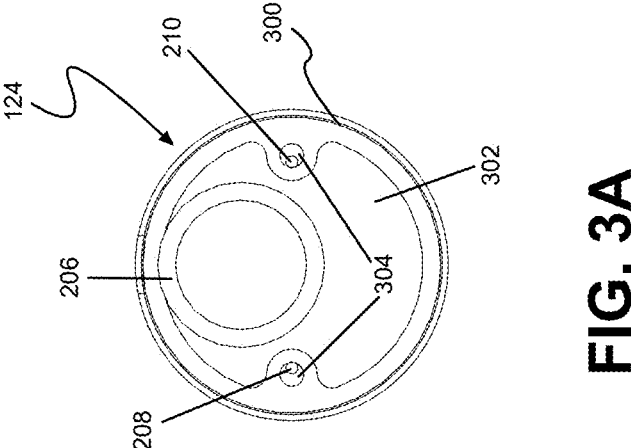
FIG. 3A is a cross-sectional end view of the flexible tip portion of FIG. 1, consistent with implementations described herein.

FIG. 3A is a cross-sectional end view of flexible tip 124 portion of endoscope shaft 110 consistent with implementations described herein. As shown, flexible tip 124 includes an outer wall 300, a main lumen 302, and two pull wire lumens 304. Main lumen 302 is sized to accommodate the internal components of shaft 110, which include a working channel 206 (FIGS. 2A/2B) and any wiring necessary for the operation of camera module 314 (FIG. 3B) and light source module 316 (FIG. 3B). Pull wire lumens 304 are formed on opposite sides of flexible tip 124 (i.e., 180° apart) so as to form a plane of deflection and are each sized to accommodate a respective pull wire 208/210 (FIG. 2A).

FIGS. 3B and 3C are isometric views of distal end 118 of endoscope shaft 110 in partially assembled and assembled configurations, respectively. As shown, distal end 118 includes flexible tip 124, an image capturing sub-assembly 306, and coupling rings 308.

In addition to lumens 302/304 described above, flexible tip 124 further includes a pair of opposing (i.e., 180° apart) longitudinally spaced webs 310. In addition to being positioned 180° relative to each other, each web 310 is further positioned 90° relative to its respective pull wire lumen 304. The above-described relationship between webs 310 and pull wire lumens 304 allows for symmetric in-plane bi-directional articulation.

Consistent with embodiments described herein webs 310 are formed by laser cutting the extruded polymer material of flexible tip 124. However, given that flexible tip 124 is such a small thin-walled polymer part, a traditional laser cutting system is not capable of cutting such a part without melting the polymer. Accordingly, webs 310 are formed by using an ultrashort, pulse laser system.

By forming flexible tip 124 in the manner described above (e.g., polymer extruded profile with subsequent laser cut webs), tip 124 may be produced with drastically lower manufacturing costs than that available using other manufacturing techniques, which is particularly advantageous when producing single-use (i.e., disposable) devices. In addition, such manufacturing techniques allow for use of a larger range of polymer material families and grades in contrast to other manufacturing methods.

Image capturing sub-assembly 306 includes a housing 312, camera module 314, and light source module 316. Housing 312 may include a length of substantially cylindrical polymeric material that includes a plurality of apertures therein for receiving camera module 312, light source module 316 and working channel 206. In one implementation, an outside diameter of housing 312 may be sized to fit within an inside diameter of a distal coupling ring 308. Furthermore, during assembly of endoscope 102, housing 312 may be secured, e.g., via adhesive (e.g., Loctite®, etc.) to the distal coupling ring 308. Consistent with embodiments described herein, the components of image capturing sub-assembly 306 may be potted with a curable adhesive, such as an ultraviolet light curable adhesive, after assembly.

In some embodiments, each of housing 312 and coupling rings 308 may be keyed, as shown in FIGS. 3A and 3B, to prevent twisting of housing 312 relative to coupling ring 308 during assembly. Furthermore, in some implementations, camera module 314 and light source module 316 may be formed as part of a circuit board assembly, such as a printed circuit board assembly (PCBA), flexible printed circuit board assembly (FPCBA), or rigid flexible printed circuit board assembly (RFPCBA) (not shown). In one implementations, the PCBA (or FPCBA/RFPCBA) may be configured to couple camera module 114 and light source module 116 to data interface assembly 205 via electrical wires 214 (FIG. 2B) that extend the length of endoscope 102. In alternative embodiments, camera module 314 and light source module 316 may be coupled directly to wires 214 and may not be integrated with or coupled to a PCBA. In yet another implementation (not shown), camera module 314 may be integrated within or provided as an additional long flexible PCBA that extends directly from the camera module 314 to data interface assembly 205, without the need for discrete electrical wires. Such an implementation may exhibit additional resistance to damage during use.

As shown in FIG. 3C, image capturing sub-assembly 306, flexible tip 124, and coupling rings 308 are encased by an outer sheath 318. Consistent with embodiments described herein, outer sheath 318 is formed of a heat shrinkable, flexible material that, when cured, flexibly seals webs 310 and couplings 308 and bonds to shaft 110.

Figure 4:
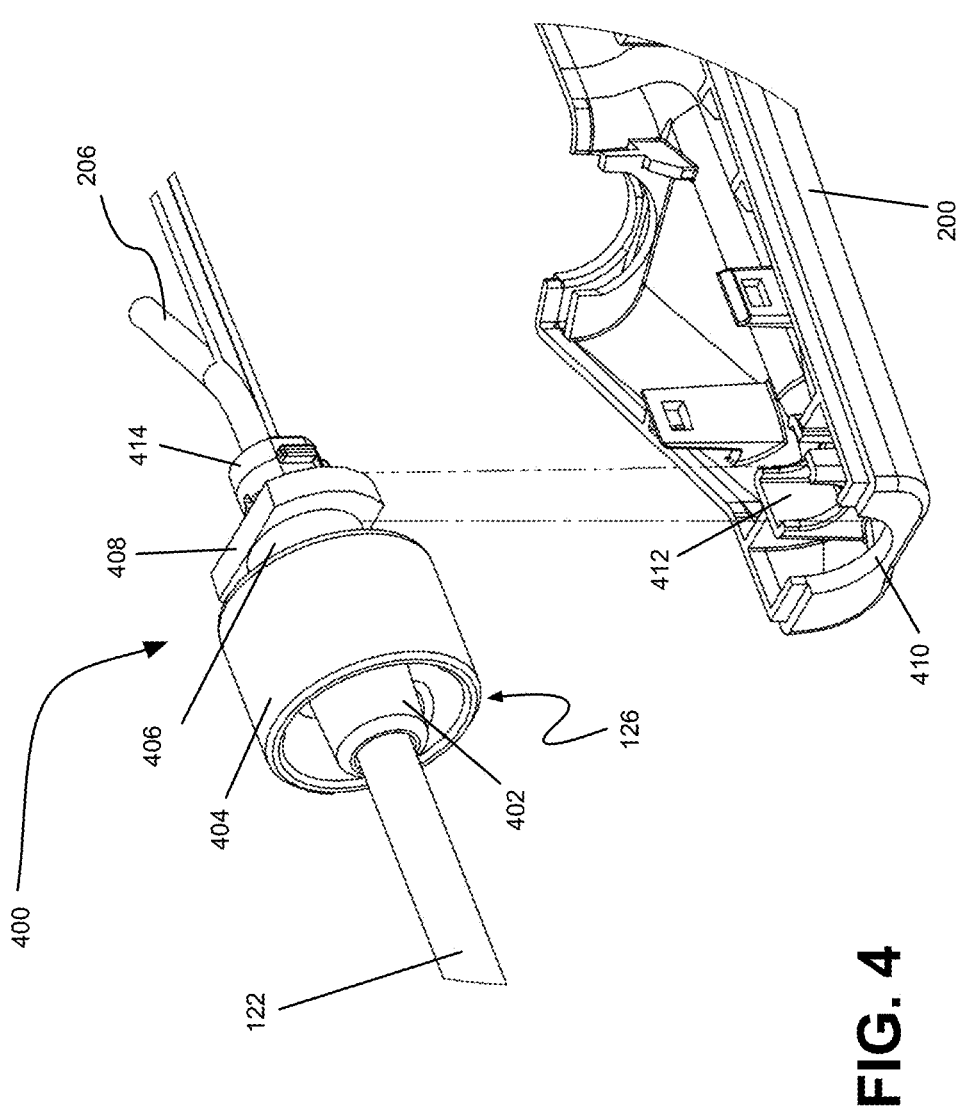
FIG. 4 illustrates an exploded, isometric, and partially cross-sectional view of an interface between a proximal end of the shaft of FIG. 1 and the right shell of FIGS. 2A-2C.

Turning now to handle 108 and proximal end 122 of shaft 110, FIG. 4 illustrates an exploded, isometric, and partially cross-sectional view of an interface between proximal end 122 of shaft 110 and right shell 200 of handle 108. As shown, proximal end 122 of shaft 110 includes tube engagement portion 126 and handle interface portion 400. Consistent with implementations described herein, tube engagement portion 126 includes an arrangement of a generally concentric first inner tube 402 and a second outer tube 404 joined at a portion (not shown) proximal to handle 108. Outer tube 404 is sized to receive and engage a device tube, such as an ET tube, for subsequent deployment into the patient's body. Accordingly, tube engagement portion 126 may include different sizes or combinations of sizes (e.g., inside and outside diameters) of each tube 402/404 consistent with a device tube to be deployed.

Regardless of size or relative size, in each embodiment of tube engagement portion 126, inner tube 402 includes a central aperture 402 formed therethrough sized to receive proximal end 122 of shaft 110. During assembly of endoscope 102, proximal end 122 may be secured, e.g., via adhesive, overmolded, interference fit, etc. to tube engagement portion 126. Outer tube 404 may be sized to receive an outside surface of the device tube. As described herein, the outside diameter of inner tube 402 is sized smaller than the inner surface of a suitable device tube, so that only outer tube 404 engages the device tube.

In some implementations, inner surface of outer tube 404 may include engagement features, such as ribs, detents, bumps, etc. (not shown in FIG. 4) to aid in releasably engaging an outer diameter of a device tube. Furthermore, in some embodiments, as shown in FIG. 4, forward edges of inner tube 402 and/or outer tube 404 may be chamfered so as to more easily receive a device tube slide along shaft 110. Consistent with embodiments described herein, all or some of tube engagement portion 126 may be formed of a resilient or semi-rigid material, such as a polymer or rubber, suitable for frictionally engaging a device tube and retaining the tube in an engagement position during initial use of endoscope 102 (e.g., insertion into a patient cavity).

As shown in FIG. 4, handle interface portion 400 is configured to positively engage corresponding portions of handle 108 to restrict or prevent rotation of shaft 110 relative to handle 108 upon assembly. For example, as shown, handle interface portion 400 may include neck portion 406 and flat-sided collar portion 408 for engaging a corresponding collar portion 410 and collar cavity 412 of right shell 200 and left shell 202 (as shown in FIGS. 2B and 2C). Furthermore, handle interface portion 400 may further include a tubular shaft entry portion 414 that includes a central aperture therethrough (not directly shown in the Figures) that is aligned with central aperture 402 of inner tube 402. The central aperture in tubular shaft entry portion 414 may be sized similarly to the opening through proximal end 122 of shaft 110, so that components (e.g., pull wires 208/210, electrical wires 214, and working channel 206) introduced through tubular shaft entry portion 414 may easily pass into shaft 110, or vice-versa. During assembly, handle interface portion 400 may be seated within right shell 200 and clamped between right shell 200 and left shell 202.

Returning to FIGS. 2A-2C, right shell 200 and left shell 202 of handle 108 each includes an outer surface 216 that include respective periphery portions 218/220. As shown, outer surface 216 is generally ergonomically shaped to be easily gripped within a user's hand. In some implementations, outer surfaces 216 of respective shells 200/202 may form substantially mirror images of each other, although in other implementations, outer surfaces 216 may vary so as to form right handed or left handed versions. Respective periphery portions 218/220 of shells 200/202 are configured to align during assembly to form an inner cavity 222 between the right shell 200 and the left shell 202. As shown in FIGS. 2A-2C, when right and left shells 200/202 of handle 108 are joined, external openings are provided for receiving shaft 110, control lever 112, suction valve assembly 114, access portion assembly 116, and data interface assembly 205, as described in additional detail below, where appropriate. In some embodiments, shells 200/202 may be formed of a plastic or other rigid material via, for example, injection molding, 3D printing, vacuum molding, etc.

As described below, inner cavity 222 may receive portions of suction valve assembly 114, access port assembly 116, control wheel assembly 204, working channel 206, and pull wires 208/210. Consistent with implementations described herein, shells 200 and 202 may be secured together via a plurality of clips spaced about periphery portions 218/220, as shown in FIGS. 2B and 2C. In other embodiments, shells 200/202 may be secured in other ways, such as via adhesives, welding, straps, screws, etc.

As shown in FIGS. 2A and 2B, access port assembly 116 is configured for insertion between right shell 200 and left shell 202 during assembly and operatively couples an external device, such as a medication drip, surgical instrument, etc. to working channel 206. Consistent with embodiments described herein, working channel 206 may include an inner and outer layer of polymer material with a polymer or metal coil layer provided therebetween in a generally helical or braided geometry. Such a configuration prevents working channel 206 from kinking during articulation and further prevents working channel 206 from collapsing when vacuum is applied (as described below).

Figure 5B:
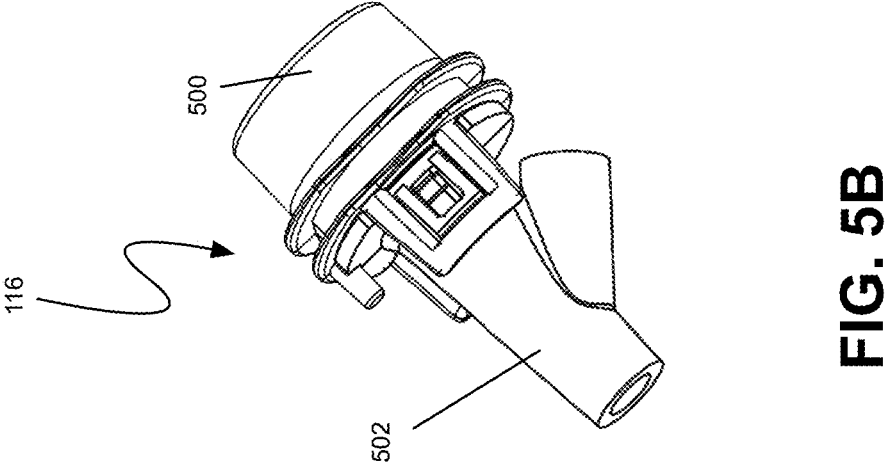
FIGS. 5A and 5B are exploded and cross-sectional detailed views of the access port assembly of FIG. 1, consistent with embodiments described herein.
Figure 5A:
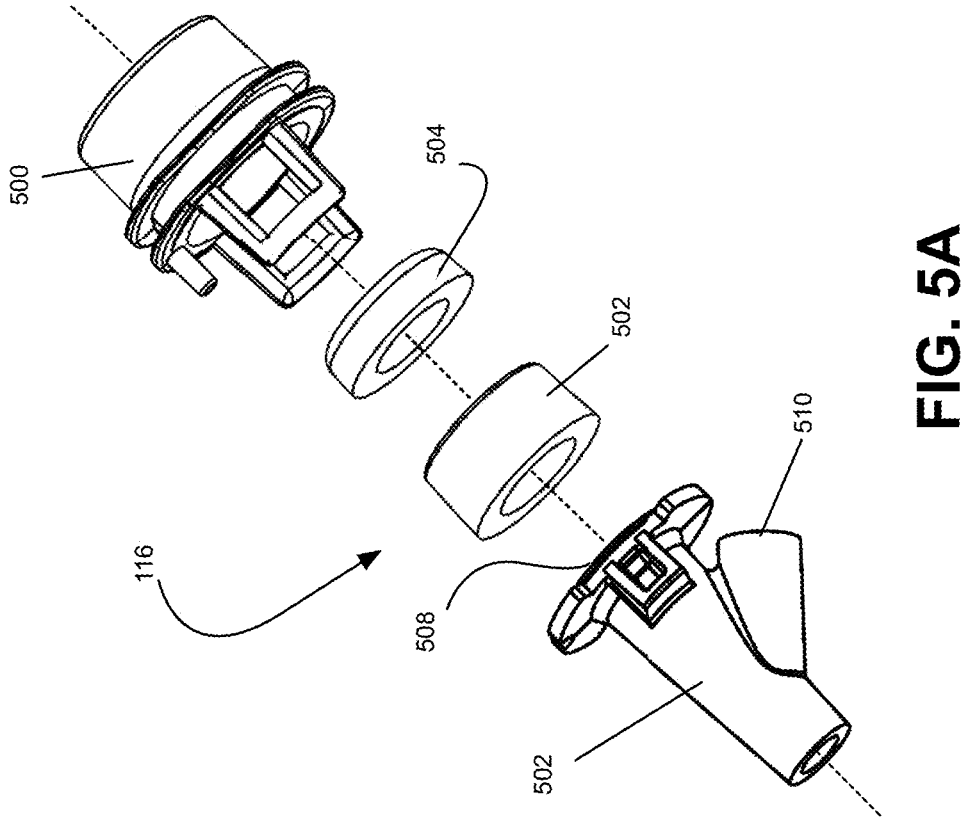

FIGS. 5A and 5B are exploded and cross-sectional detailed views of access port assembly 116 consistent with embodiments described herein. As shown in FIG. 5A, access port assembly 116 includes a housing 500, a tube fitting portion 502, and seal portions 504 and 506. Housing 500 is a generally tubular structure formed of a rigid or semi-rigid material and includes engagement features that correspond to engagement structures provided in right and left shells 200/202. For example, as shown in FIG. 2B, housing 500 includes a peripheral channel configured to engage generally u-shaped projections in right and left shells 200/202.

Tube fitting portion 502 includes a substantially hollow structure formed of a rigid or semi-rigid material (e.g., a plastic). As shown, tube fitting portion 502 includes a first inlet 508, a second inlet 510, and an outlet 512. First inlet 508 is aligned with and sized for receipt within housing 500 during assembly. Furthermore, as shown in FIG. 2B, first inlet 508 is configured to provide external access to working channel 206 via housing 506 and seals 502/504. Second inlet 510 is configured to receive an internal suction connector 224 (FIGS. 2A and 2B) that is coupled to section assembly 116, which is described in detail below in relation to FIGS. 6A and 6B. Outlet 512 is oriented and sized to receive a proximal end of working channel 206.

Seal portions 502/504 are formed of a resilient material and include respective apertures aligned with first inlet 508 and housing 500. The size of the respective apertures is consistent with the potential uses for access port assembly, such as corresponding to particular sizes of medical tubing, instrument diameters, etc. Seal 502 is normally closed, and therefore allows for suction functionality as described below to occur entirely from the distal end of the working channel 206. Seal 504 provides an airtight seal with accessories such as a luer lock connector (e.g., syringe) or similar when used in the access port assembly 116, while seal 502 is opened by such accessories to gain access to working channel 206. This functionality, for example, enables connecting a syringe into the access port assembly 116 so that fluids can be administered into the working channel 206 without leakage.

Figure 6A:
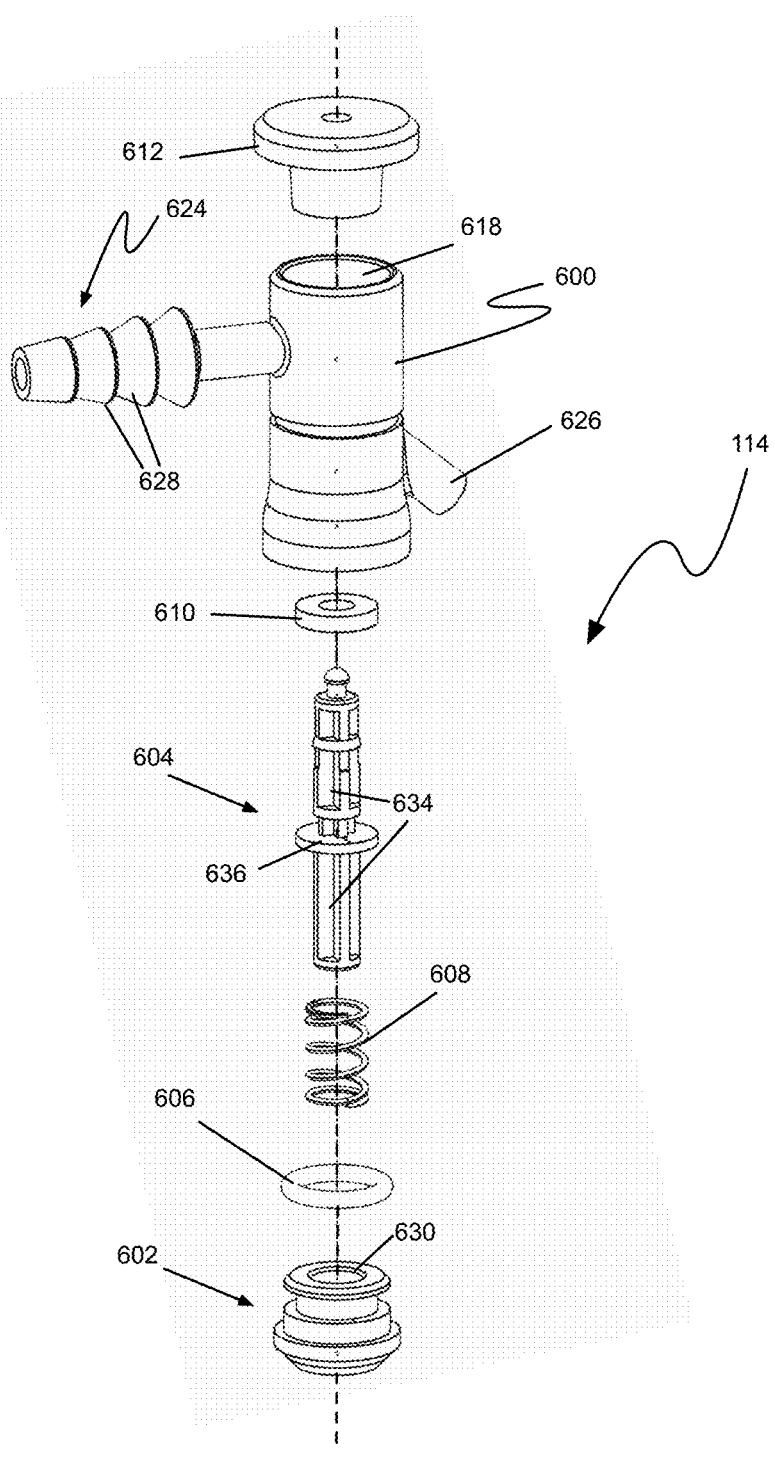
FIG. 6A is an exploded detailed view of the suction valve assembly of FIG. 1, consistent with embodiments described herein.
Figures 6B, 6C:
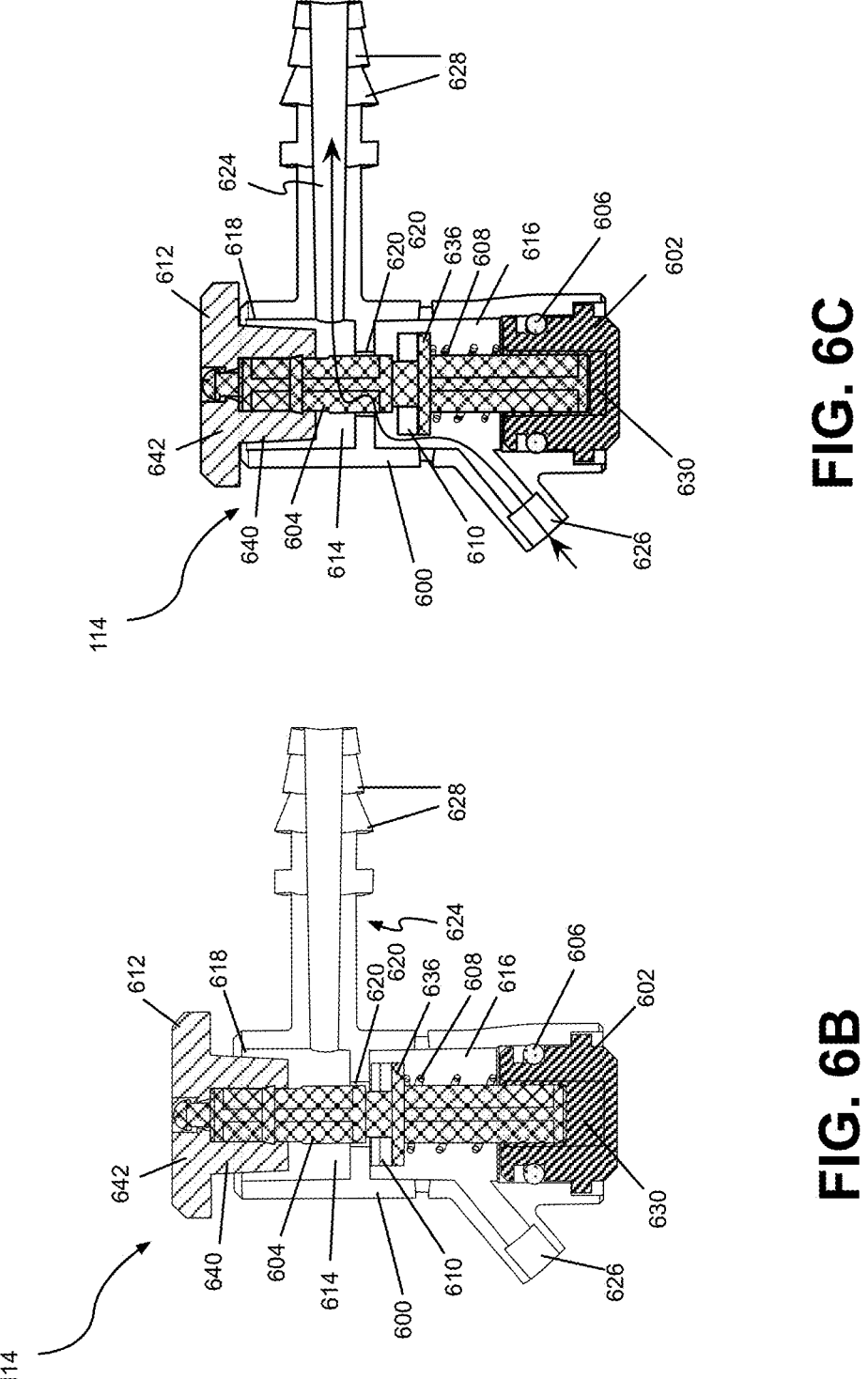
FIGS. 6B and 6C are cross-sectional detailed views of the suction valve assembly of FIG. 6A in closed and open states, respectively.

As shown in FIGS. 2A and 2B, suction valve assembly 114 is also configured for insertion between right shell 200 and left shell 202 during assembly and operatively couples an external source of suction to working channel 206 via suction connector 224 and tube fitting 502 described above. FIG. 6A is an exploded detailed view of suction valve assembly 114 consistent with embodiments described herein. FIGS. 6B and 6C are cross-sectional detailed views of suction valve assembly 114 in closed and open states, respectively. As shown in FIG. 6A, suction valve assembly 114 includes a housing 600, bottom cover 602, plunger 604, O-ring seal 606, spring 608, washer seal 610, and valve button 612.

Housing 600 is a generally tubular structure formed of a rigid or semi-rigid material and includes engagement features that correspond to engagement structures provided in right and left shells 200/202. For example, as shown in FIG. 2A, housing 600 includes a peripheral channel in an intermediate portion thereof configured to engage a generally u-shaped projection in right and left shells 200/202. During assembly, suction valve assembly 114 is placed between right and left shells 200/202.

As shown in FIGS. 6B and 6C, housing 600 further includes an upper chamber 614, a lower chamber 616, an upper aperture 618, a central aperture 620, a lower aperture 622, an outlet 624, and an inlet 626. Outlet 624 is fluidly coupled with upper chamber 614, while inlet 626 is fluidly coupled with lower chamber 616. Upper and lower chambers 614/616 are fluidly coupled by central aperture 620, which is sized to allow plunger 604 to move therethrough, as described below. Outlet 624 is configured to project outwardly from housing 600 adjacent upper chamber 614 to receive a source of negative pressure (suction). As shown in FIG. 6A, an outer surface of outlet 624 may include a plurality of ribs or barbs 628 for engaging and sealing with a suction tube that is pushed thereon. Inlet 626 is configured project outwardly from housing 600 adjacent lower chamber 616 and sized to receive a proximal end of suction connector 224 therein, as shown in FIGS. 2A and 2B.

Bottom cover 602 is configured to be received within and enclose lower chamber 616 and includes a central cavity 630 therein for receiving a lower portion of plunger 604 during actuation of valve 114. Furthermore, as shown in FIGS. 6B and 6C, bottom cover 602 further includes a groove or channel 632 for receiving O-ring seal 606, which prevents suction from affecting other components in the interior of handle 108.

Plunger 604 is a movable, elongated structure configured to extend through upper and lower chambers 614/616 and pass through central aperture 620. As shown in FIG. 6A, plunger includes a series of channels 634 formed in an outer periphery thereof which allow air to pass efficiently around plunger 604 when valve 114 is actuated. Plunger 604 further includes a shoulder portion 636 for engaging washer seal 610 on an upper surface thereto to prevent suction from reaching lower chamber 616 when valve is in the normally closed state (FIG. 6B). Spring 608 is positioned between a lower surface of shoulder portion 636 and bottom cover 602 and is configured to bias plunger 604 into the closed state.

Valve button 612 engages an upper end of plunger 604 and includes a lower portion that is received within upper aperture 618. When in the closed state (FIG. 6B), a space or gap 636 formed between valve button 612 and housing 600 allows any suction from outlet 624 to be applied outside of endoscope 102 via upper chamber 614 and upper aperture 618, while washer seal 610 prevents the suction from being applied to lower chamber 616 and inlet 626. Conversely, when valve button 612 is depressed, plunger 604 moves downwardly with respect to housing 600, thereby moving washer seal 610 away from central aperture 620, and thereby allowing negative pressure to be applied to lower chamber 616 and inlet 626. Release of valve button 612 causes plunger 604 to return to the closed position by virtue of spring 608. Consistent with embodiments described herein, valve button 612 includes a lower portion and an upper portion 640 and an upper portion 642 that extends radially outwardly with respect to lower portion 640. As shown in FIGS. 6C, a bottom surface of upper portion 642 is configured to seal upper aperture 618 when valve assembly 114 is in the closed state.

To control the articulation of flexible tip 124, pull wires 208 extend through shaft 120 proximal and intermediate portions 122/120 of shaft 110 and couple to control wheel assembly 204. More particularly, in one implementation, as shown in FIGS. 2A and 2B, proximal ends of pull wires 208 and 210 are secured to termination elements 209 and 211, respectively. As described more fully below, termination elements 209 and 211 may include generally cylindrical or disc-shaped elements configured to be received and retained within control wheel assembly 204. Termination elements 209 and 211 may be formed of any suitable material, such as plastic, a metal, etc. and may be secured to pull wires 208 and 210 in any suitable manner, such as via welding, an adhesive, soldering, brazing, crimping, etc. Furthermore, although not depicted in the Figures, distal ends of pull wires 208/210 may be secured within distal ends of pull wire lumens 304. As described herein, by enabling accurate tensioning of pull wires 208/210 during assembly, positional accuracy of each pull wire termination element 209/211 on its respective pull wire 208/210 is irrelevant, since manufacturing tolerance variation can be accounted for independently during tensioning.

Figures 7A, 7B:
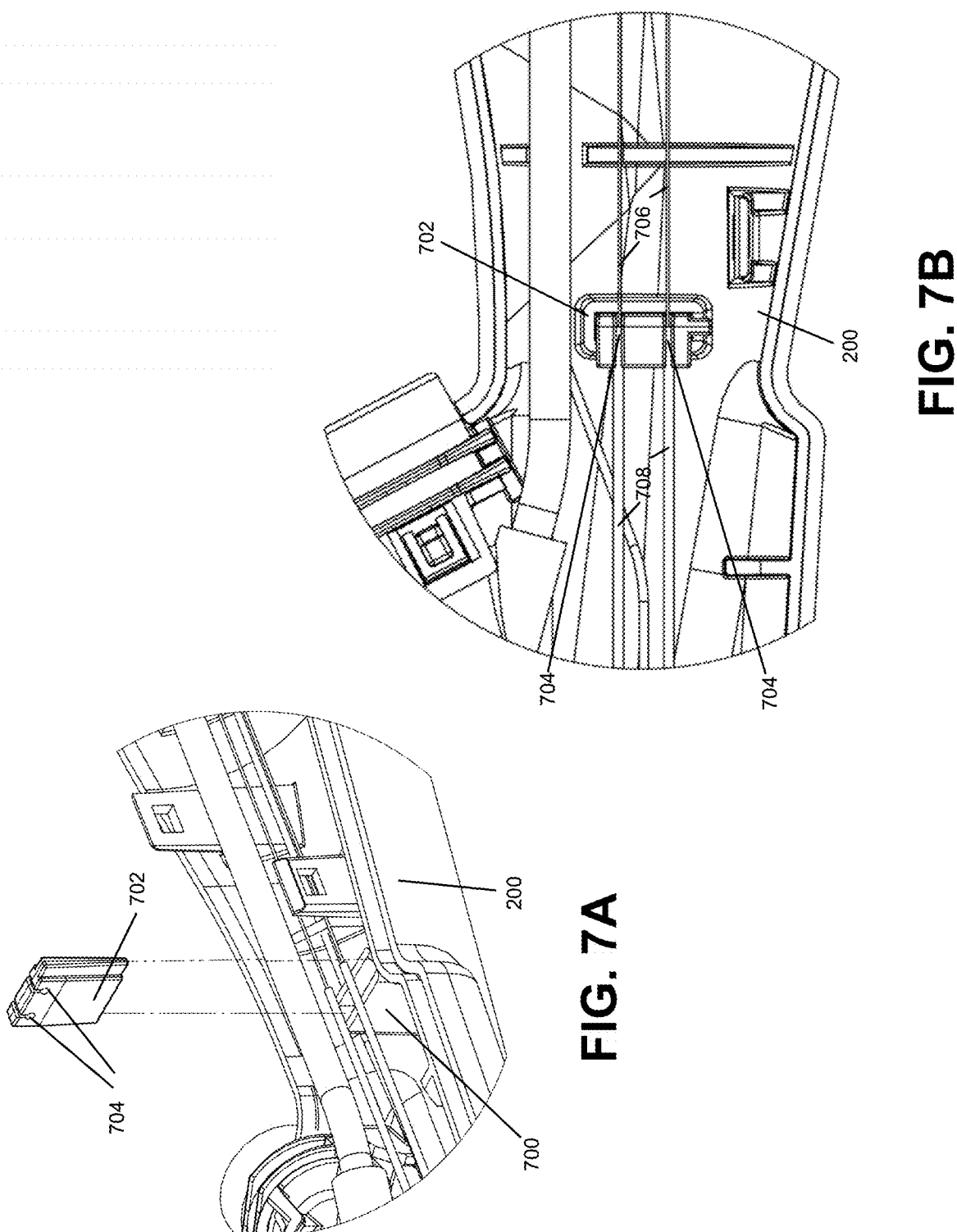
FIGS. 7A and 7B are detailed partially exploded and cross-sectional views, respectively, illustrating a portion of the right shell of FIGS. 2A-2B.

FIGS. 7A and 7B are detailed partially exploded and cross-sectional views, respectively, illustrating a portion of right shell 200. As shown, right shell 200 is provided with a coil stop receptacle 700 positioned generally along a center line of right shell 200 (e.g., aligned with the central aperture of tubular shaft entry portion 414) and sized to securely receive a coil stop 702. In some embodiments, coil stop receptacle 700 is formed integrally with right shell 200, while in other embodiments, coil stop receptacle 700 is formed separately and is secured to right shell 200 during assembly or manufacture, such as via adhesive, welding, screws, etc.

Coil stop 702 is formed of a resilient or semi-rigid material and is sized to fit within coil stop receptacle 700 and be retained therein via a friction fit. As shown in FIG. 7A, coil stop 702 includes a pair of slots 704 formed in a top surface thereof for receiving pull wires 208/210. As shown in FIGS. 7A and 7B, consistent with embodiments described herein, each pull wire 208/210 includes a Bowden-style cable having an inner wire 706 an outer compression coil (which is an incompressible spring) 708. Compression coil 708 extends between coil stop 702 and flexible tip 124, while inner wire 706 extends between control wheel assembly 204 and flexible tip 124 distal end. A distal end of inner wire 706 extends through pull wire lumens 304 in flexible tip 124 and may be secured within the distal end of wire lumens 304, as described above. For example, distal ends of control wires 208/210 secured to the distal ends of their respective lumens 304 using a combination of flaring and adhesive, or other means of fixation.

During operation, when pull wires 208/210 are actuated either forward or backward, corresponding pull wire tension increases to enable articulation and a resultant compressive force must be transferred back to handle 108. This force transfer is accomplished by compression coil 708 taking the load and transferring back to the handle via coil stop 702. Without compression coil 708, the load would travel thru intermediate and proximal portions 120/122 of shaft 110 and may result in shaft 110 moving in an uncontrolled and or undesirable manner when tip 124 is articulated.

As shown in FIG. 7A, upon assembly, compression coils 708 are secured, e.g., via a stepped configuration, within coil stop slots 704, effectively fixing compression coils 708 to handle 108 and allowing inner wires 706 to slide therethrough. In one implementation, slots 704 may be shaped to include a cylindrical bottom portion sized commensurate with a diameter of compression coils 708 and having a narrower upper portion. Such a configuration retains compression coils 708 within slots 704 even when handle 108 is inverted or otherwise manipulated. In addition, this configuration prevents compression coils 708 do not travel toward control wheel assembly 204 during use.

Figure 8A:
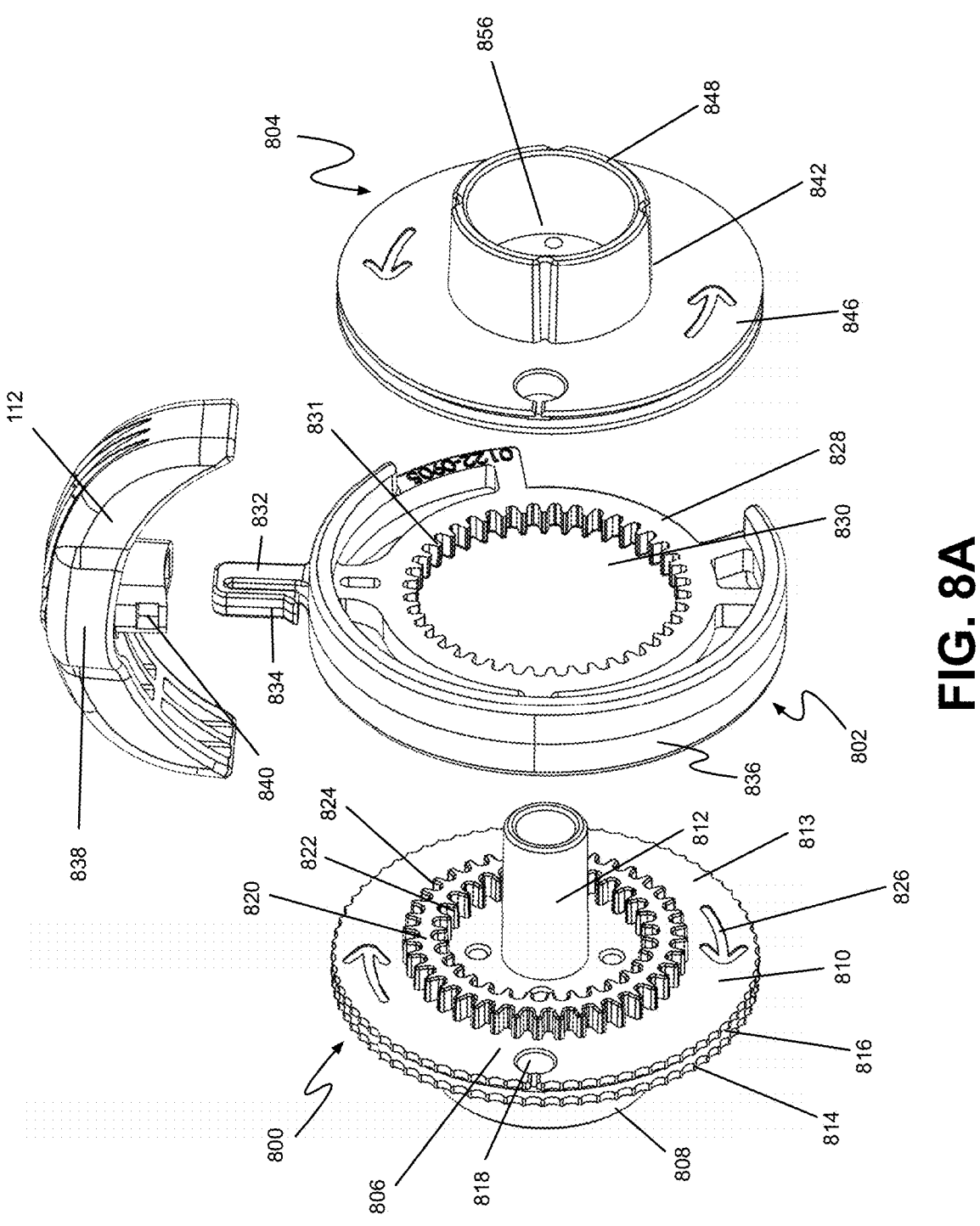
FIGS. 8A and 8B are right and left side exploded isometric views, respectively, of the control wheel assembly of FIGS. 2A-2B.
Figure 8B:
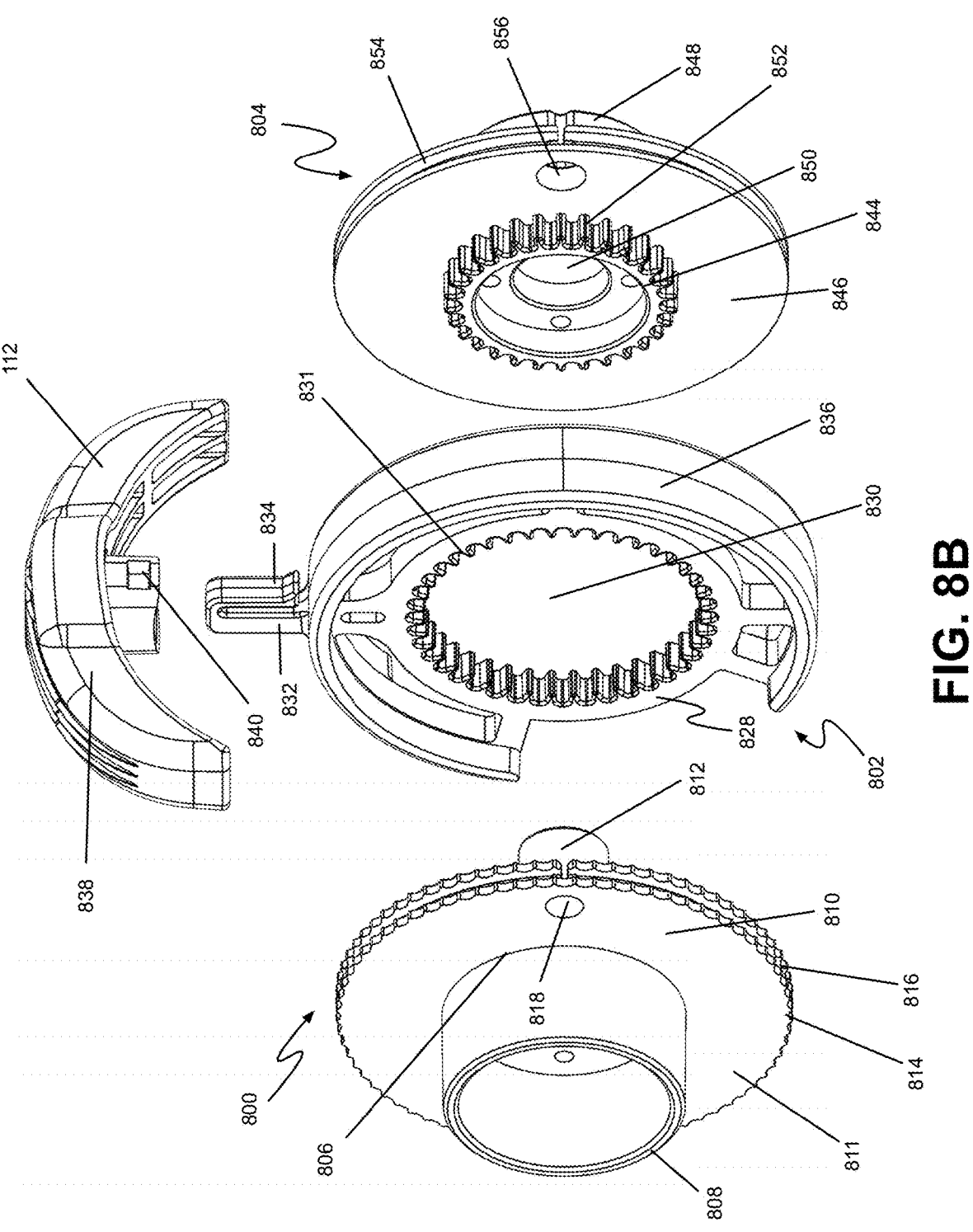

Turning now to control wheel assembly 204, FIGS. 8A and 8B are right and left side exploded isometric views, respectively, of control wheel assembly 204 and control lever 112. As shown in FIGS. 8A and 8B, control wheels assembly 204 includes a first control wheel 800, a second control wheel 802, and a third control wheel 804 aligned concentrically to enable accurate neutral tension in pull wires 208/210 during assembly of endoscope 102, as described in detail below.

As shown in FIGS. 2A and 2B, in association with control wheel assembly 204, right shell 200 includes a main control wheel boss 226, a tensioning pin boss 228, a pair of routing posts 230, and a set of routing vanes 232. It should be noted that features described herein as relating to right shell 200 may, in some embodiments, be implemented, in whole or in part, in left shell 202. Similarly, the arrangement of control wheels 800/804 may be similarly reversed.

Main control wheel boss 226 is a tubular body that projects inwardly from right shell 200 and receives a corresponding central shaft 808 of first control wheel 800 therein, such that first control wheel 800, when assembled, rotates within main control wheel boss 226. As shown in FIG. 2A, main control wheel boss 226 may be formed integrally with right shell 200. Similar to main control wheel boss 226, tensioning pin boss 228 is a cylindrical body that also projects inwardly from right shell 200 in a spaced relationship to main control wheel boss 226. As described below, tensioning pin boss 228 is configured to receive, during assembly of endoscope 302, a tensioning pin (not shown) that engages a serrated outer periphery of first control wheel 800 to prevent first control wheel 800 from freely rotating about main control wheel boss 226 during assembly and tensioning of pull wires 208 and/or 210.

Routing posts 230 project inwardly from right shell 200 in a spaced relationship about a longitudinal axis of right shell 200 and include an arcuate configuration for guiding pull wires 208/210 and preventing unnecessary wear or binding. Routing vanes 232 likewise project inwardly from right shell 200 and, in one exemplary embodiment, include a set of three longitudinal vanes 232a, 232b, and 232c that together form two substantially v-shaped slots 234a and 234b. As best shown in FIG. 2A, during assembly, when pull wires 208 and 210 are positioned within right shell 200, pull wire 208 is placed within v-shaped slot 234a and pull wire 210 is placed within v-shaped slot 234b. Pull wires 208 and 210 are then routed around the arcuate shape of routing posts 230 such that pull wire 208 is positioned to one side of main control wheel boss 226 (e.g., an upper side relative to the orientation of FIG. 2B) and pull wire 210 is positioned to the opposite side of main control wheel boss 226 (e.g., a lower side relative to the orientation of FIG. 2B). As described below, first control wheel 800 and third control wheel 804 are configured to receive respective pull wires 208/210 along outer peripheries thereof, respectively, as described in additional detail below.

As shown in FIG. 2C, left shell 202 includes a secondary control wheel boss 227. Secondary control wheel boss 227 is a tubular body that projects inwardly from left shell 202 and receives a corresponding central shaft of third control wheel 804 thereon, such that third control wheel 804, when assembled, rotates around secondary control wheel boss 227. Additionally, as described below, secondary control wheel boss 227 further includes an inside aperture for receiving a central shaft of first control wheel 200. As shown in FIG. 2C, secondary control wheel boss 227 may be formed integrally with left shell 202.

As shown in FIGS. 8A and 8B, first control wheel 800 comprises a generally cylindrical body 806 including first central shaft 808, a central flange region 810, and a second central shaft 812. As briefly described above, first central shaft 808 is sized for receipt within main control wheel boss 226. Central flange region 810 projects radially outwardly from first central shaft 808 and includes a planar outer surface 811 that slidingly engages main control wheel boss 266. Central flange region 810 further includes an outer periphery that includes a plurality of teeth or serrations 814. As briefly described above, serrations 814 are configured to engage tensioning pin boss 228 during assembly to prevent free rotation of first control wheel 800 relative to main control wheel boss 226/right shell 200. In addition to serrations 814, the outer periphery of central flange region 810 also includes an annular groove 816 and a wire fixing aperture 818. Annular groove 816 is configured to receive one of pull wires 208/210 (shown as control wire 208 in FIG. 2A) and wire fixing aperture 818 is configured to receive one of pull wire termination elements 209/211 (shown as termination element 209 in FIG. 2A).

During assembly, after first central shaft 808 is placed within main control wheel boss 226, pull wire termination element 209 may be initially inserted into wire fixing aperture 818. As shown in FIG. 8B, wire fixing aperture 818 may include a wire entry slot to facilitate entry of termination element 209 and pull wire 208 into wire fixing aperture 818. Once termination element 209 is seated within wire fixing aperture 818, first control wheel 800 may be rotated (e.g., clockwise relative to right shell 200) to route pull wire 208 into annular groove 816. As described above, the free rotation of first control wheel 800 is restrained by engagement of serrations 814 with tensioning pin boss 228. In some implementations, such rotation is performed by hand during assembly. However, in other implementations, an automated or computer-controlled device may be used to rotate control wheel and to introduce a proper and uniform tension to pull wire 208 by means of angular tip measurements, tension measurement, or torque measurement.

As shown in FIG. 8B, an inner surface 813 of central flange region 810 includes a generally cylindrical multi-purpose engagement ring 820 that projects inwardly therefrom. Each of the radial inward surface 822 and the radial outward surface 824 of engagement ring 820 of comprise toothed or notched configurations for engaging, respective portions of second control wheel 802 and third control wheel 804. The size/pitch of the teeth/notched features on inward surface 822 and outward surface 824 dictate how accurately tensioning can be achieved. That is, more accurate precision may be achieved with finer gear teeth. However, this precision is balanced against the need to withstand appropriate load during articulation. As best shown in FIG. 8B, inner surface 813 of central flange region 810 may include indicia (e.g., arrows) 826 for indicating a direction that an assembler should rotate first control wheel 800 to achieve proper tensioning of pull wire 208.

Second central shaft 812 of first control wheel 800 projects inwardly from central flange region 810 concentrically with first central shaft 808. As shown in FIG. 2A and described in additional detail below, second central shaft 812 is configured to receive a central aperture in third control wheel 804 to affect concentric alignment of third control wheel 804 with first control wheel 800 (and second control wheel 804).

As shown in FIGS. 8A and 8B, second control wheel 802 comprises a generally tubular body member 828 having a central aperture 830 provided therethrough. Consistent with embodiments described herein, central aperture 830 may be provided with a toothed or notched inner surface 831 configured to matingly engage radial outward surface 824 of multi-purpose engagement ring 820. Upon assembly, rotational movement of second control wheel 802 (e.g., caused by movement of control lever 112) causes first control wheel to rotate, thus causing control wire 208 to move longitudinally within handle 108 and shaft 110, and affecting a corresponding deflection of tip 124, as described above.

Second control wheel 802 further includes a control lever engagement portion 832. As shown in FIGS. 8A and 8B, control lever engagement portion 832 projects radially from second control wheel 802. Upon assembly, control lever engagement potion 832 is configured to extend at least partially outside of handle 108, via control lever opening 236 (as shown in FIGS. 2A-2C). In some embodiments, control lever engagement portion 832 includes a resilient clip or hook portion 834 for engaging a corresponding clip portion in control lever 112 (described below). In addition, consistent with embodiments described herein, second control wheel 802 may include an arcuate member 836 configured to project from a portion of body member 828 that functions to prevent or minimize the entry of foreign materials into inner cavity 222 via control lever opening 236. The inner side of arcuate member 836 also mates with/covers both annular grooves 816/854 when fully assembled together, which prevents pull wires 208/210 from falling out of grooves 816/854 when respective pull wires 208/210 are not in tension. As shown, arcuate member 836 includes a generally tubular configuration that is positioned radially between the control lever engagement portion 832 and the body member 828 and that has a width that is wider than control lever opening 236.

As shown in FIG. 8B, control lever 112 may include a generally T-shaped body 838 configured for easy forward/backward manipulation by a user's thumb during operation of endoscope 102. In some embodiments, T-shaped body 838 includes a curved lateral profile that generally mirrors an outer configuration of handle 108. Such a feature minimizes the likelihood that control lever 112 will get caught up on various environmental elements, such as clothing, equipment, wires/cables, etc. An outer surface of control lever 112, may include a friction surface, such as ribbed, grooved, or knurled surface. Such a configuration reduces the likelihood that a user's thumb will slip off of control lever 112 during use.

Although a T-shaped body is shown in the figures, in other embodiments, additional or alternative configurations may be used, such as a generally cylindrical or bulbous knob. As described above, control lever 112 includes a clip portion 840 configured to enable removable coupling of control lever 112 with control lever engagement portion 832.

As shown in FIGS. 8A and 8B, third control wheel 804 comprises a generally cylindrical body 842 including an engagement ring portion 844, a central flange region 846, and a central shaft 848. As shown in FIG. 8A, cylindrical body 842 includes a central aperture 850 provided therethrough. As briefly described above, central aperture 850 in body 842 is configured to concentrically receive an end of second central shaft 812 of first control wheel 800 during assembly. Engagement ring portion 844 of third control wheel 804 projects axially inwardly from the body 842 and includes a radially outward surface 852 that includes a toothed or notched configuration for engaging radially inward surface 822 of engagement ring 820 of first control wheel 800. This mating notched relationship causes third control wheel 804 to rotate in response to movement of control lever 112.

Central flange region 846 of third control wheel 804 projects radially outwardly from body 842 and includes a planar, axially inward surface for engaging a corresponding portion of second control wheel 802. Central flange region

846 further includes an outer periphery that includes an annular groove 854 and a wire fixing aperture 856. Similar to annular groove 816 in first control wheel 800 described above, annular groove 854 is configured to receive one of pull wires 208/210 (shown as control wire 210 in FIG. 2A) and wire fixing aperture 856 is configured to receive one of pull wire termination elements 209/211 (shown as termination element 211 in FIG. 2A).

During assembly, pull wire termination element 211 may be initially inserted into wire fixing aperture 856. As shown in FIG. 8B, wire fixing aperture 856 may include a wire entry slot to facilitate entry of terminal element 211 and pull wire 210 into wire fixing aperture 856. Once terminal element 211 is seated within wire fixing aperture 856, central aperture 850 may be placed loosely onto second central shaft 812 of first control wheel 800, in a spaced relationship relative to engagement ring 820 of first control wheel 800. Once termination element 211 is seated within wire fixing aperture 856, and third control wheel 804 is placed loosely onto first control wheel 800, third control wheel 804 may be rotated (e.g., counter-clockwise relative to right shell 200) to route pull wire 210 into annular groove 854, the rotation occurs about second central shaft 812 of first control wheel 800 and central aperture 850 of third control wheel 804. After appropriate tension has been applied to pull wire 210 to render articulating tip 124 initially at a neutral position (i.e., no longitudinal deflection), third control wheel 804 may be fully seated on first control wheel 800, such that outward surface 852 of engagement ring 850 positively mates with radially inward surface 822 of engagement ring 820 of first control wheel 800, thereby locking the first, second and third control wheels 800-804 together. In this configuration, second central shaft 812 of first control wheel 800 projects through central aperture 850 in third control wheel body 842 and extends concentrically within second central shaft 812 of third control wheel 804.

Second central shaft 812 of first control wheel 800 projects inwardly from central flange region 810 concentrically with first central shaft 808. As shown in FIG. 2A and described in additional detail below, second central shaft 812 is configured to receive a central aperture in third control wheel 804 to affect concentric alignment of third control wheel 804 with first control wheel 800 (and second control wheel 804).

As shown in FIG. 8B, central shaft 848 of third control wheel 804 includes a generally tubular configuration having an inside surface 856 therein. As described above, during assembly, second central shaft 812 projects into central shaft 848. The relationship between inside surface 856 of central shaft 848 and the outside surface of second central shaft 812 of first control wheel 800 is configured to receive secondary control wheel boss 227 therebetween, upon assembly of left shell 202 to right shell 200.

In some alternative implementations, less than three control wheels may be used. For example, the features and functions provided by second control wheel 802 (e.g., an attachment mechanism for control lever 112, etc.) may be integrated into one or more of control wheels 800/804. In this manner, independent tensioning of control wheels 800/804 may be maintained.

By providing for independent and secure tensioning of each pull wire 208/210 independently, during assembly, fine, smooth articulation control may be realized, without the inherent slack or "play" provided by known control mechanisms. Furthermore, as described above, assembly of endoscope may be performed without the need for special equipment or tools.

Although manual tensioning and articulation is generally described above and illustrated in the Figures, in other implementations, control wheel assembly 204 may include or support electrical tensioning and/or control. For example, a small electric motor (e.g., a servo motor) could be implemented to engage toothed outward surface 824 of engagement ring 820. Alternative, the electric motor may be configured to engage first central shaft 808. In such an implementation, the motor may be mounted to right shell 200 adjacent to or in lieu of main control wheel boss 226. Control of such a motor could be performed using one or more switches or actuators mounted on device handle 108.

As briefly described above, in some implementations, endoscope 102 may be a single use or disposable device. As such, it may be beneficial to simplify the components of endoscope 102 to reduce the cost of the device. In particular, consistent with embodiments described herein, endoscope system 100 may include alternative processing capabilities that decrease the cost and complexity of the disposable portion, e.g., endoscope 102.

Figure 9:
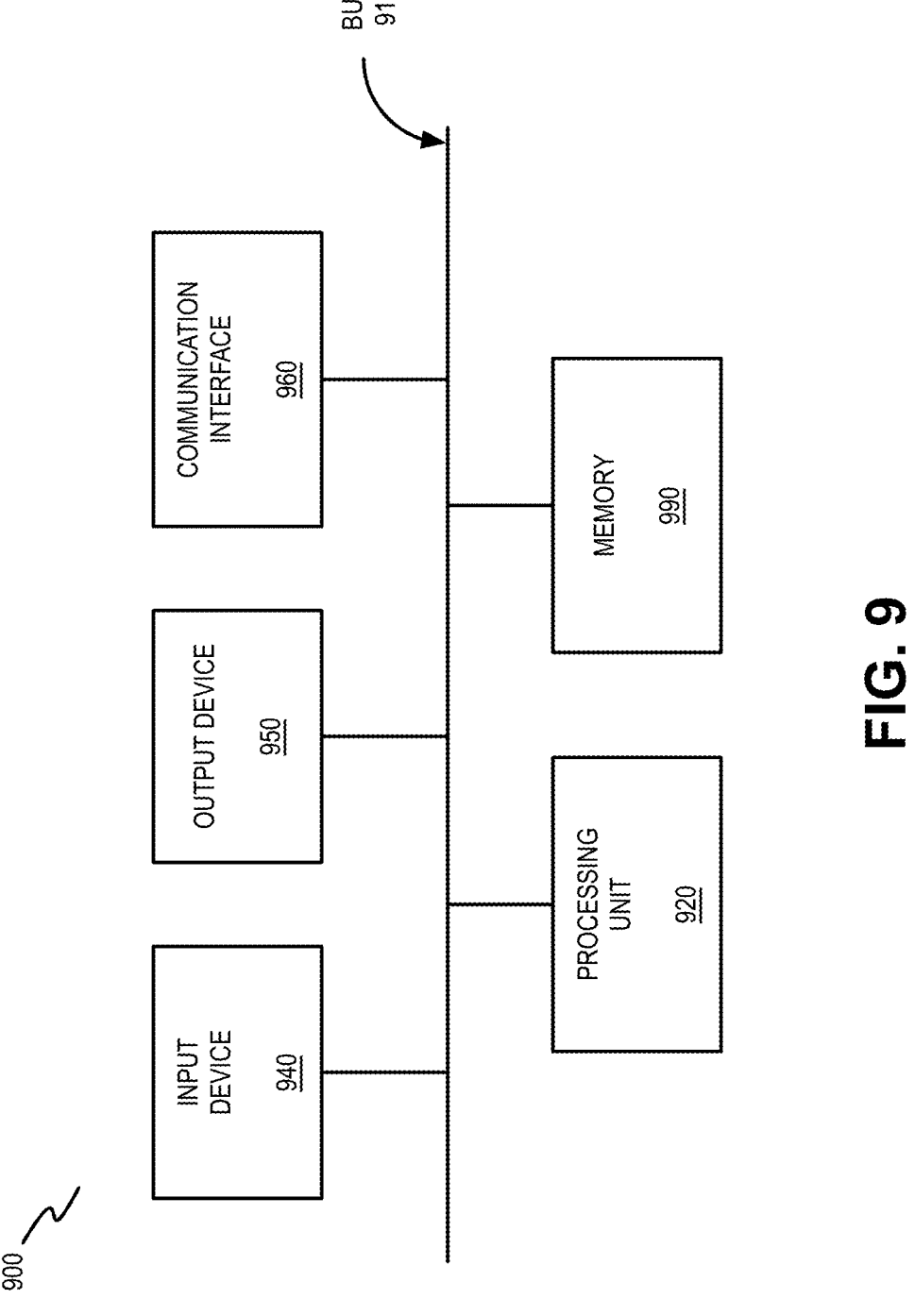
FIG. 9 illustrates a simplified exemplary configuration of one or more components of the laryngoscope system of FIG. 1.

FIG. 9 illustrates a simplified exemplary configuration of one or more components 900 of endoscope system 100, such as endoscope 102, data cable 104, and video monitor 106. Referring to FIG. 9, component 900 may include bus 910, a processing unit 920, a memory 930, an input device 940, an output device 950, and a communication interface 960. Bus 910 may include a path that permits communication among the components 900 of endoscope system 100. In one exemplary implementation, bus 910 may include an I²C bus which supports a master/slave relationship between components 900. As described below, in exemplary implementations, the master and slave roles may be negotiated between the components, or alternatively, between multi-use devices, such as data cable 104 and video monitor 106.

Processing unit 920 may include one or more processors, microprocessors, or processing logic that may interpret and execute instructions. Memory 990 may include a random access memory (RAM) or another type of dynamic storage device that may store information and instructions for execution by processing unit 920. Memory 990 may also include a read only memory (ROM) device (e.g., an electrically erasable and programmable ROM (EEPROM)) or another type of static storage device that may store static information and instructions for use by processing unit 920. In other embodiments, memory 990 may further include a solid state drive (SSD).

Input device 940 may include a mechanism that permits a user to input information to endoscope system 100, such as a keyboard, a keypad, a mouse, a pen, a microphone, a touch screen, voice recognition and/or biometric mechanisms, etc. Output device 950 may include a mechanism that outputs information to the user, including a display (e.g., a liquid crystal display (LCD)), a data interface assembly (e.g., port), a printer, a speaker, etc. In some implementations, a touch screen display may act as both an input device and an output device. In the endoscope system 100 depicted in FIG. 1, only video monitor 106 may be provided with input device 940 and output device 950, however in other implementations, one or more other components of endoscope system 100 may include such devices. As depicted in FIG. 1, endoscope 102 and data cable 104 may be implemented as headless devices that are not directly provided with input device 940 or output device 950 and may receive commands from, for example, video monitor 106.

Communication interface 960 may include one or more transceivers that endoscope system 100 (e.g., video monitor 106) uses to communicate with other devices via wired, wireless or optical mechanisms. For example, communication interface 960 may include a modem or an Ethernet interface to a local area network (LAN) or other mechanisms for communicating with elements in a communication network (not shown in FIG. 1). In other embodiments, communication interface 960 may include one or more radio frequency (RF) transmitters, receivers and/or transceivers and one or more antennas for transmitting and receiving RF data via a communication network, such as a wireless LAN or Wi-Fi network.

The exemplary configuration illustrated in FIG. 9 is provided for simplicity. It should be understood that endoscope system 100 may include more or fewer components than illustrated in FIG. 9. In an exemplary implementation, endoscope system 100 performs operations in response to one or more processing units 920 executing sequences of instructions contained in a computer-readable medium, such as memory 990. A computer-readable medium may be defined as a physical or logical memory device. The software instructions may be read into memory 990 from another computer-readable medium (e.g., a hard disk drive (HDD), SSD, etc.), or from another device via communication interface 960. Alternatively, hard-wired circuitry may be used in place of or in combination with software instructions to implement processes consistent with the implementations described herein. Thus, implementations described herein are not limited to any specific combination of hardware circuitry and software.

Figure 10:
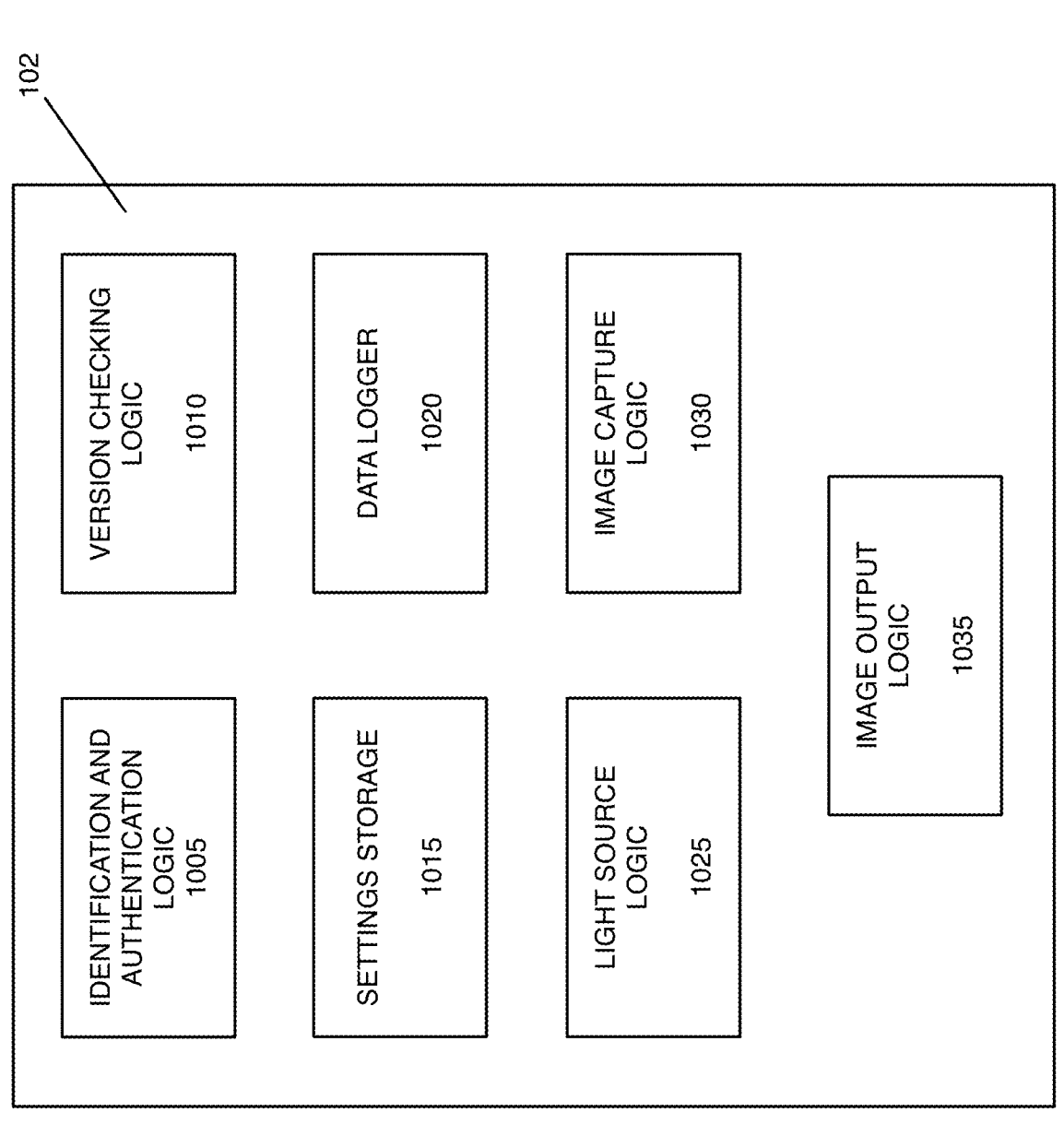
FIG. 10 is an exemplary functional block diagram of components implemented in a single-use laryngoscope blade consistent with embodiments described herein.

FIG. 10 is an exemplary functional block diagram of components implemented in a single-use endoscope 102 in accordance with an embodiment described herein. In the embodiment of FIG. 10, all or some of the components may be implemented by processing unit 920 executing software instructions stored in memory 990.

As shown, endoscope 102 may include identification and authentication logic 1005, version checking logic 1010, settings storage 1015, data logger 1020, light source logic 1025, image capture logic 1030, and image output logic 1035.

Identification and authentication logic 1005 is configured to, upon power up of endoscope 102, exchange identification and authentication information with data cable 104 and/or video monitor 106. For example, endoscope 102 may communicate identification information to data cable 104 via bus 910 (e.g., the I²C bus). In one embodiment, the identification information may comprise information relating to the type of endoscope 102, such as the size, application, model, particular video format, etc. In other implementations, the identification information may include information specific to the particular endoscope 102, such as serial number or other uniquely identifying information.

Consistent with embodiments described herein, identification and authentication logic 1005 may provide the identifying information to data cable 104 and video monitor 106 for use in determining whether endoscope 102 is authorized for use with the data cable 104 and video monitor 106. For example, as described below, upon receipt of the identification information from endoscope 102, the data cable 104 and/or video monitor 106 may determine whether the endoscope 102 is authorized for use. In this manner, unauthorized, third party endoscopes may be monitored, logged, or potentially disallowed by the endoscope system described herein.

Furthermore, in other embodiments, identification and authentication logic 1005 may be configured to exchange usage information stored in data logger 1020 with video monitor 106 via data cable 104. For example, data logger 1020 may be configured to record details regarding usage (e.g., power up) of the endoscope 102, such as date, time, and duration of endoscope 102. Identification and authentication logic 1005 may, during subsequent power ups, transmit this information to video monitor 106 to for use in determining whether the endoscope 102 may be properly used. For example, single-use endoscope 102 may only be authorized for power-up a predetermined (e.g., <5) number of times, to ensure that the scope is not used outside of its intended purpose. For reusable endoscopes, the usage information stored in data logger 1020 may be used to provide historical information, reconditioning recommendations, etc. In other embodiments, the information may be used to monitor a time between uses, to determine whether appropriate sterilization procedures have been followed.

Version checking logic 1010 is configured to, in coordination with similar logic in data cable 104 and video monitor 106, determine which component has a most recently updated set of camera settings. For example, because components of medical devices may not be upgradable in the field, providing an integrated upgrade path between the separate components (e.g., separate components released at different times) provides an efficient manner for rolling out updated camera settings using only a single factory-updated component, without requiring a dedicated field update process for all components within the system.

Consistent with embodiments described herein, upon power up of system 100, version checking logic 1010 determines which of endoscope 102, data cable, 104, or video monitor 106 maintains the most recently updated set of camera settings in settings storage 1015. If endoscope 102 is not the device with the most recently updated set of camera settings, the device having such settings may transmit the camera settings to endoscope 102 or otherwise make the settings available to image capture logic 1030.

As described briefly above, in one embodiment, endoscope 102, data cable, 104, and video monitor 106 may be coupled via an I²C bus, which requires that only one device be in the "master" role at any one time. Generally, since the main control of system 100 is initiated by video monitor 106, video monitor 106 is typically in the "master" role. However, consistent with embodiments described herein, upon system power up, each of video monitor 106, data cable 104, and/or endoscope 102 may alternatively assume the "master" role for the purposes of sharing information regarding its set of camera settings.

Light source logic 1025 is configured to cause light source module 316 to become illuminated in accordance with settings stored in settings storage 1015 or received from video monitor 106.

Image capture logic 1030 is configured to capture images via camera module 314 based on the most recently updated set of camera settings identified and stored in settings storage 1015 and/or received from video monitor 106. The captured images are then forwarded to image output logic 1035 for relay to video monitor 106. More specifically, image capture logic 1030 is configured to receive image capture control commands from video monitor 106 via data cable 104. In response to an image capture command, image capture logic 1030 captures images based on image capture settings stored in settings storage 1015. Depending on whether endoscope 102 is single-use or reusable, image output logic 1035 may be integrated within endoscope 102 or may include multiple components included within endoscope 102 and data cable 104.

Figure 11:
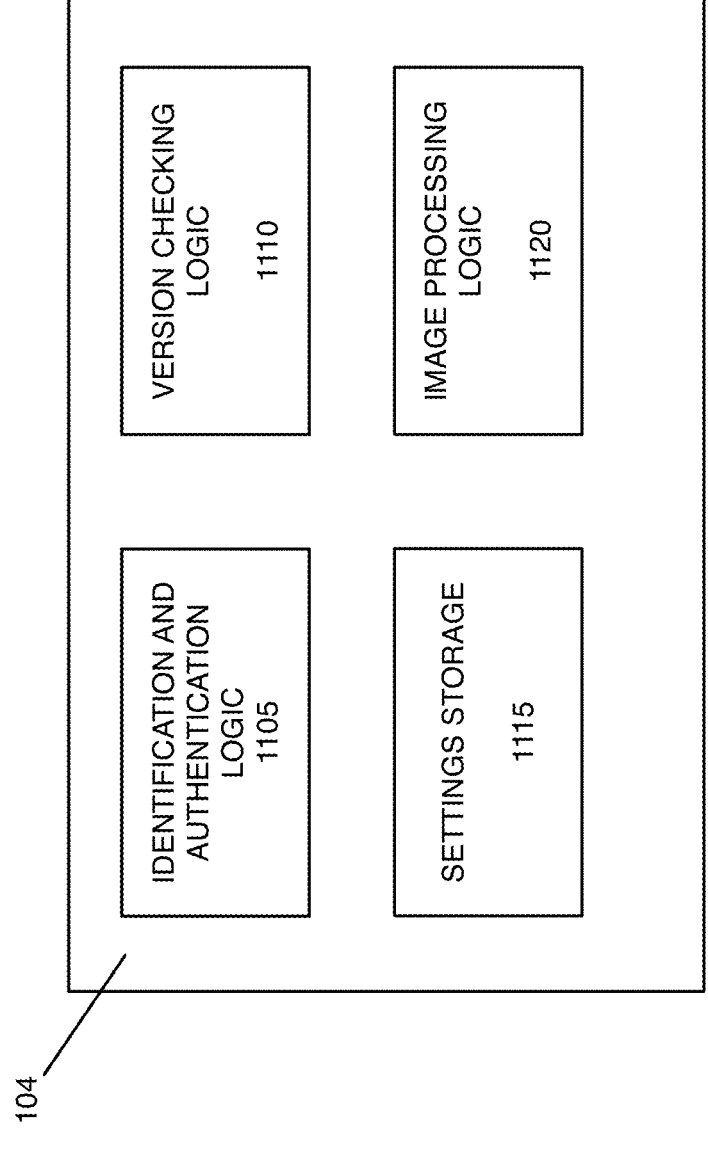
FIG. 11 is an exemplary functional block diagram of components implemented in a data cable consistent with embodiments described herein.

FIG. 11 is an exemplary functional block diagram of components implemented in a data cable 104 in accordance with an embodiment described herein. In the embodiment of FIG. 11, all or some of the components may be implemented by processing unit 920 executing software instructions stored in memory.

As shown, data cable 104 may include identification and authentication logic 1105, version checking logic 1110, and settings storage 1115 configured similarly to identification and authentication logic 1005, version checking logic 1010, and settings storage 1015 described above with respect to endoscope 102. For example, identification and authentication logic 1105 may include logic for determining an identity of a connected endoscope 102 and determining whether the endoscope 102 is suitable for use with data cable 104. In other embodiments, identification and authentication logic 1105 may be further configured to identify and appropriate video path between endoscope 102 and video monitor 106.

Version checking logic 1110 includes logic for determining which of data cable 104, video monitor 106, and/or endoscope 102 has the most up-to-date set of camera settings corresponding to the identified endoscope 102. As described above in relation to version checking logic 1010, version checking logic 1110 is similarly configured to alternatively transmit an indication of the version of the set of camera settings stored in settings storage 1115 to each of video monitor 106 and endoscope 102 and similarly receive corresponding information from each of video monitor 106 and endoscope 102. When it is determined that the version of the set of camera settings stored in settings storage 1115 is the most up-to-date, version checking logic 1110 may provide the settings to image capture logic 1030, which may then apply to camera module 316 and/or light source module 314 in endoscope 102.

Data cable 104 may further include image processing logic 1120 that performs some or all of the image processing on images captured by camera module 314/316. In one embodiment, image processing logic 1120 may include a serializer and/or related logic for preparing images captured by camera module 314/316 for transmission to, compatibility with, and display by video monitor 106. In addition, image processing logic 1120 may include logic for providing scaling and padding or modification of other image attributes of captured images prior to transmission to video monitor 106.

Figure 12:
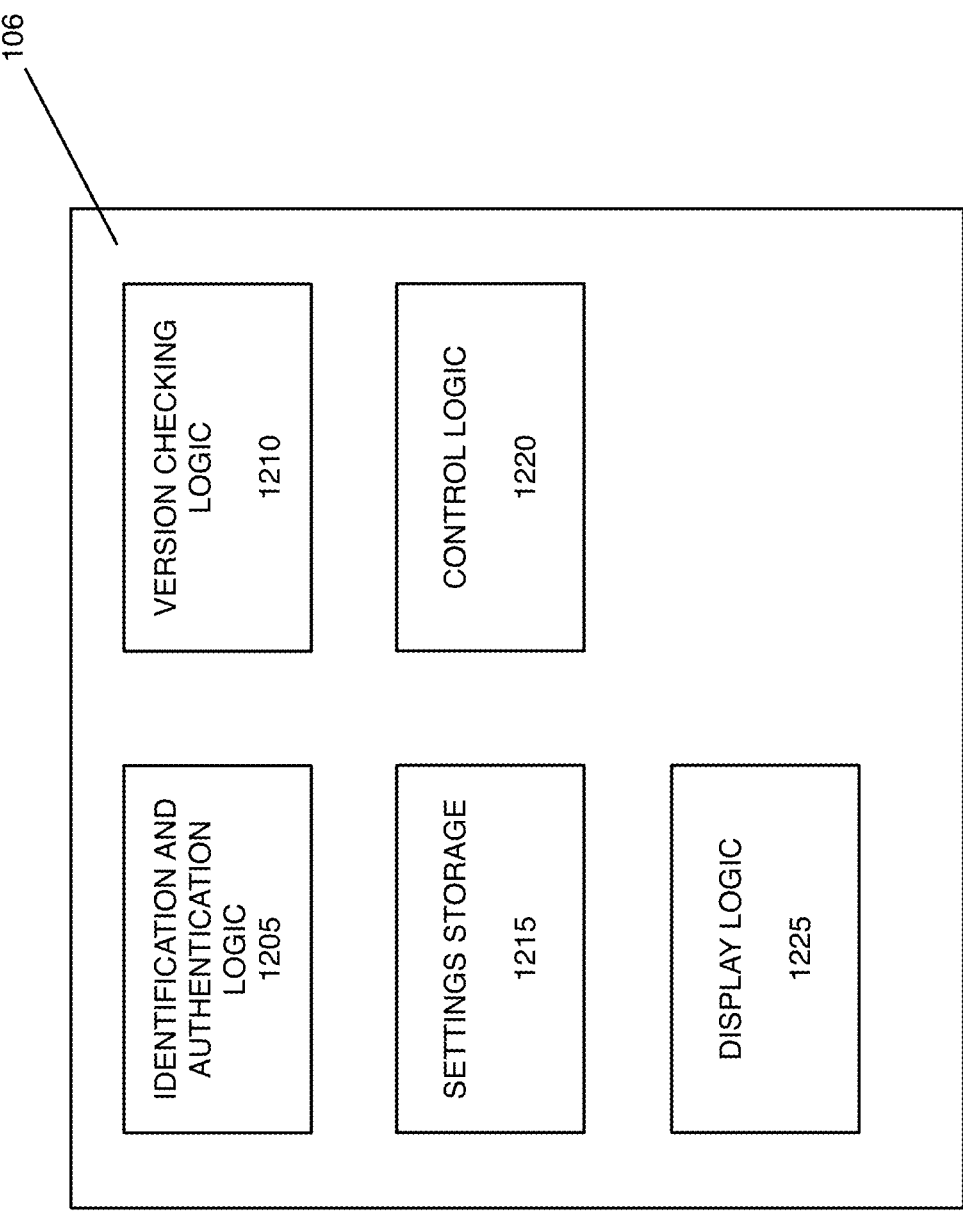
FIG. 12 is an exemplary functional block diagram of components implemented in a video monitor consistent with embodiments described herein.

FIG. 12 is an exemplary functional block diagram of components implemented in a video monitor 106 in accordance with an embodiment described herein. In the embodiment of FIG. 12, all or some of the components may be implemented by processing unit 920 executing software instructions stored in memory 990.

As shown, video monitor 106 may include identification and authentication logic 1205, version checking logic 1210, settings storage 1215, control logic 1220, and display logic 1225. Identification and authentication logic 1205, version checking logic 1210, and settings storage 1215 may be configured similarly to identification and authentication logic 1005/1105, version checking logic 1010/1110, and settings storage 1015/1115 described above with respect to endoscope 102 and data cable 104. For example, identification and authentication logic 1205 may include logic for determining an identity of a connected endoscope 102 and determining whether the data cable 104 and endoscope 102 is suitable for use with video monitor 106.

Version checking logic 1210 includes logic for determining which of data cable 104, video monitor 106, and/or endoscope 102 has the most up-to-date set of camera settings corresponding to the identified endoscope 102. As described above in relation to version checking logic 1010, version checking logic 1210 is similarly configured to alternatively transmit an indication of the version of the set of camera settings stored in settings storage 1215 to each of data cable 106 and/or endoscope 102 and similarly receiving corresponding information from each of video monitor 106 and endoscope 102 before resuming the "master" role on bus 910 (e.g., the I²C bus). When it is determined that the version of the set of camera settings stored in settings storage 1215 is the most up-to-date, version checking logic 1210 may provide the settings to image capture logic 1030 in endoscope 102.

After version checking logic 1210 completes its check, control logic 1220 receives user commands to commence image capture, such as via control pad 124. Display logic 1225 receives the image data or video signal from endoscope 102 via data cable 104. As described above, in some implementations, portions of the processing of the image data may be performed by image processing logic 520 in data cable 104.

Consistent with embodiments described herein, the most up-to-date camera settings stored in one of settings storage 1015, 1115, or 1215, may include camera settings optimized for capturing the most useful images in an intra-airway environment. Such an environment typically exhibits the following characteristics: 1) extremely confined field of view, typically having no more than a 3"×3" near circular cavity within which to operate; 2) no primary ambient environmental lighting; all lighting relies on a fixed single point background light emitted by light source module 314 provided immediately adjacent to camera module 316; 3) extreme red spectrum color bias; 4) frequent extreme swings in lighting brightness caused by unpredictable intrusion of objects into camera field of view when combined with the small usage environment; and 5) high contrast with both near-field and far-field points of interest. Unfortunately, conventional camera settings are not optimized for such an environment and, consequently, images or video quality may suffer, and/or pertinent visual details may be lost.

As described above, camera module 316 comprises a CCD or CMOS device. Consistent with embodiments described herein, camera module 316 may include configurable programming registers that allow the image capturing characteristics of camera module 316 to be optimized. Settings storage 1015, 1115, and/or 1215 in one or more of endoscope 102, data cable 104, and video monitor 106 may be programmed to include one or more sets of customized camera module or image processing logic register values to optimize image and/or video quality in intra-airway environments. For example, different sets of customized camera module or image processing logic register values may be stored for different identified endoscope, such as different length tubes shafts, different tip sizes, etc. etc.

Modern camera modules generally include automatic gain control (AGC) and/or automatic exposure control (AEC), which are designed to improve image quality by automatically boosting the gain and increasing the exposure in low light images so that objects can be seen more clearly and reduce the gain and decrease the exposure in bright images to avoid the subject of the image from being washed out or blurry. Unfortunately, in intra-airway environments or other internal environments, occluding elements, such as the patient's tongue, or other organs or tissue, etc. may briefly block the camera view causing the AGC/AEC to reduce the gain and decrease the exposure time, thereby losing far field details, which may be necessary for accurate insertion of the endoscope or placement of a corresponding ETT.

Consistent with embodiments described herein, camera module registers or settings relating to the control of AGC and AEC may be optimized. In particular, a setting relating to an upper limit of an AGC/AEC stable operating region may be modified. The upper limit of the AGC/AEC stable operating region refers to how high or bright an incoming image or video signal must become before the camera's gain algorithm mutes or attenuates the signal, by a preset amount, before sending the signal to video monitor 106. Accordingly, consistent with described embodiments, the upper limit of the AGC/AEC stable operating region may be raised (from its default) so that the "trigger point" of upper limit gain attenuation does not occur until the incoming signal significantly increases. The consequence is that any intruding near-field object, such as a patient's tongue or a medical intubation tube, would need to either block a larger portion of the field of view or remain in the field of view much longer.

Consistent with embodiments described herein, a setting relating to the lower limit of the AGC/AEC stable operating region may also be modified. This setting controls how low or dim an incoming signal must achieve before the camera's gain algorithm boosts the signal sent to host. Because a primary objective for intra-airway image capture is to ensure that a patient's far-field vocal cords are visible most of the time during an intubation procedure, the value for the lower limit of the AGC/AEC stable operating region may be increased (from its default) to consequently maintain the "window" in which attenuation is active to a minimum.

In some embodiments, one or more settings relate to or identify the maximum gain boost that can be applied when the incoming signal drops below the AGC/AEC lower limit. As described above, since the AGC/AEC lower limit is raised in accordance with the described embodiments, the effect is that gain boost would be triggered at gain amounts higher than traditionally applied. This may cause images to overexpose even at moderate lighting levels, since the lower limit was now near or above normal lighting levels. To counter this, the automatic gain ceiling maximum AGC value setting may be lowered (from its default) to limit the maximum boost that camera module 316 can apply. This helps manage the over exposure effect and bring it to an acceptable level.

Figure 13:
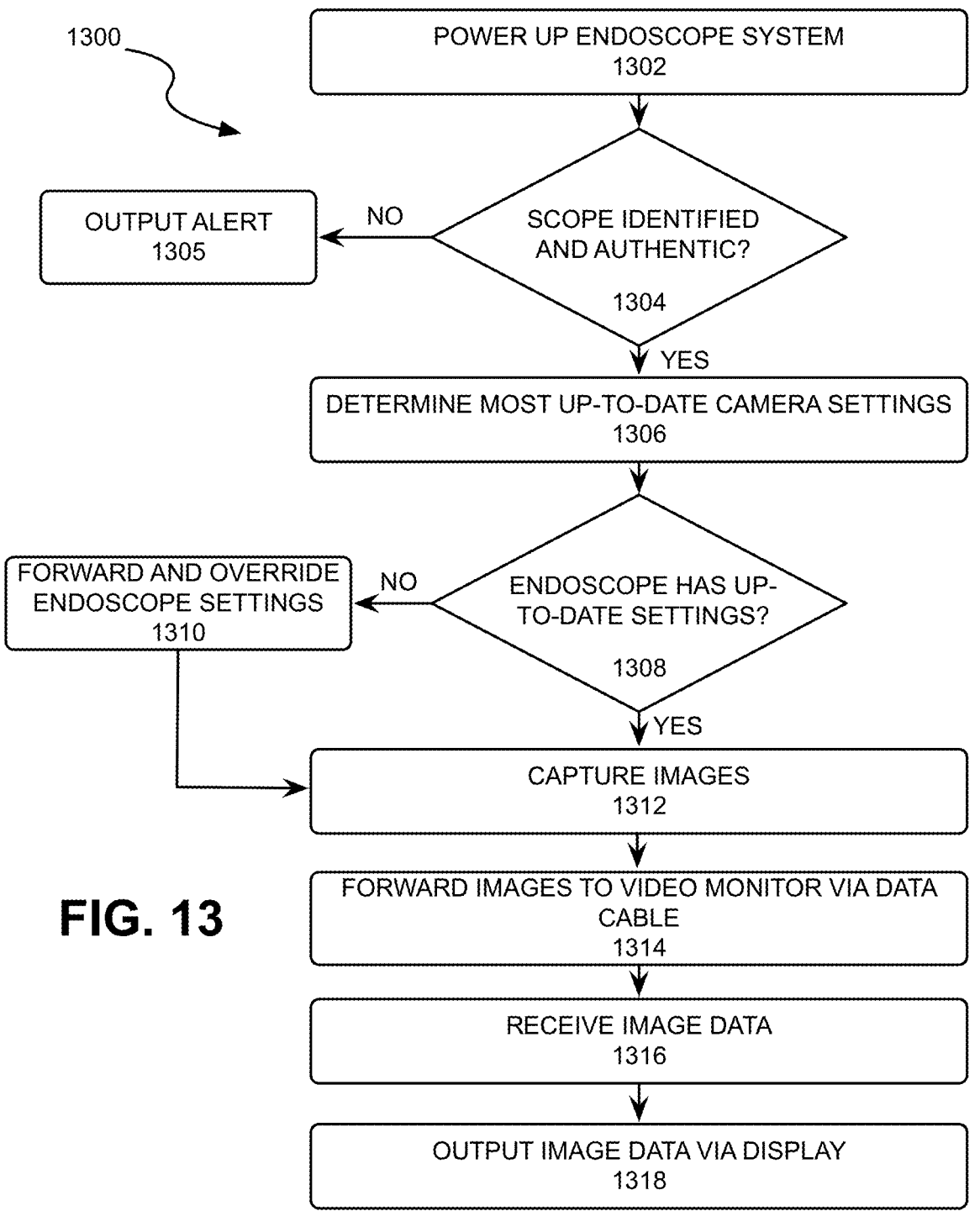
FIG. 13 is a flow diagram illustrating exemplary process for capturing images via the video laryngoscope system of FIG. 1.

FIG. 13 is a flow diagram illustrating an exemplary process 1300 for capturing images via video endoscope system 100 described herein. In one embodiment, process 1300 may begin when endoscope 102 is plugged into data cable 104, data cable 104 is plugged into video monitor 106, and video monitor 106 is powered up (block 1302).

At block 1304, data cable 104 and/or video monitor 106 identify endoscope 102 and determines whether it is authentic. For example, as described above, identification and authentication logic 605 requests and receives blade identification information from endoscope 102 and determines whether endoscope 102 is authentic and, potentially, that it has not exceeded its authorized number of uses. If not (block 1304—NO), the process may end and a notification or alert is output via video monitor 106 (block 1305). In other embodiments, unauthorized devices for which a video path can be determined may be permitted to transmit video to video monitor, and, accordingly, in such embodiments, processing for unidentified or unauthorized devices may proceed to block 1312, described below.

However, if endoscope 102 is identified and determined to be authentic (block 1304—YES), two or more of the endoscope 102, data cable 104, and video monitor 106 negotiate to determine which device has the most up-to-date camera settings relative to the identified endoscope 102 (block 1306). For example, as described above, each component may alternatively assume a "master" role on bus 910 to receive version information from the other components, which are then compared to its current version.

At block 1308, it is determined whether a device other than endoscope 102 has the most up-to-date settings. If not (block 1308—NO), the process proceeds to block 1312. However, when one of the other devices includes the most up-to-date settings, (block 1308—YES), the settings are forwarded to camera module 316 in endoscope 102 for use during image capture, which overrides any currently stored settings (block 1310).

At block 1312, image capture logic 1030 may capture images based on the settings received or verified in step 1308/1310 above. Captured images are forwarded to video monitor 106 via data cable 104 (block 1314). For example, image output logic 1035 in endoscope 102 may output the image data captured by camera module 316 to data cable 104. As described above, in some implementations, some or all image processing on the image data may be performed by image processing logic 1120 in data cable 104.

Processed image or video data is received by video monitor 106 (block 1318) and output via display 128 (block 1320).

The foregoing description of embodiments provides illustration but is not intended to be exhaustive or to limit the embodiments to the precise form disclosed. In the preceding description, various embodiments have been described with reference to the accompanying drawings. However, various modifications and changes may be made thereto, and additional embodiments may be implemented, without departing from the broader scope of the invention as set forth in the claims that follow. The description and drawings are accordingly to be regarded as illustrative rather than restrictive.

As set forth in this description and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items.

The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction described in the present application should be construed as critical or essential to the embodiments described herein unless explicitly described as such.

What is claimed is:

1. An endoscope device, comprising:
a handle having a central cavity therein;
a shaft projecting from the handle,
wherein the shaft includes a proximal portion and a distal portion relative to a flexible tip coupled to the distal portion of the shaft;
a pair of pull wires extending from the handle portion through the shaft portion and coupled to the flexible tip;
a control wheel assembly rotationally secured within the central cavity of the handle and operatively coupled to the pair of pull wires; and
a control lever coupled to the control wheel assembly via an opening in the handle,
wherein manipulation of the control lever causes rotation of the control wheel assembly, which then causes deflection of the flexible tip via the pull wires,
wherein the control wheel assembly includes an arcuate member that covers at least a portion of the control wheel assembly to prevent external contaminants from entering the central cavity of the handle via the opening adjacent the control lever,
wherein the control wheel assembly comprises at least one control wheel that includes an annular groove on a periphery thereof to receive at least one of the pair of pull wires, and
wherein the arcuate member is further configured to overlay the annular groove to prevent at least one of the pair of pull wires from coming out of the annular groove on the periphery of the at least one control wheel.

2. The endoscope device of claim 1, wherein the handle comprises a first shell and a second shell joined together to form the central cavity therein, wherein the control wheel assembly is rotationally secured within the central cavity.

3. The endoscope device of claim 2, wherein a portion of the handle proximate to the opening has a curved configuration corresponding to the control wheel assembly, wherein the opening in the handle has a first length and a first width, and wherein the arcuate member has a second length and a second width, wherein the second length of the arcuate member is longer than a first length of the opening and wherein the second width of the arcuate member is wider than the first width of the opening.

4. The endoscope device of claim 3, wherein the second length of the arcuate member extends along at least half of an outer periphery of the control wheel assembly.

5. The endoscope device of claim 1, wherein the at least one control wheel further comprises:
a first control wheel having a first annular groove and a second control wheel having a second annular groove, wherein a first pull wire of the pair of pull wires is received within the first annular groove of the first control wheel and a second pull wire of the pair of pull wires is received within the second annular groove of the second control wheel.

6. The endoscope device of claim 1, wherein the handle further comprises a pair of routing posts for directing the pair of pull wires toward the control wheel assembly.

7. The endoscope device of claim 1, wherein the each of the pair of pull wires comprise Bowden-style cables that include an inner wire and an outer compression coil, wherein the handle further comprises a coil stop for engaging the outer compression coil and transferring the compression load during articulation to the handle via the compression coil stop within the handle.

8. The endoscope device of claim 1, further comprising:
a working channel extending through the shaft,
wherein the handle further comprises an access port assembly for allowing external access to the working channel.

9. The endoscope device of claim 8, wherein the handle further comprises a suction valve assembly coupled to the access port assembly to enable selective application of negative pressure to the shaft via the working channel.

10. The endoscope device of claim 1, further comprising:
a tube engagement device adjacent a proximal end of the shaft for retaining a device tube over the shaft prior to use,
wherein the tube engagement device is configured to frictionally engage an outside diameter of the device tube.

11. An endoscope device, comprising:
a handle having a central cavity therein;
a shaft projecting from the handle,
wherein the shaft includes a flexible tip distal from the handle;
a control wheel assembly rotationally secured within the central cavity of the handle, rotation of which causes deflection of the flexible tip; and
a control lever coupled to the control wheel assembly and projecting outwardly via through an opening in the handle,
wherein the control wheel assembly includes an arcuate member that covers at least a portion of the control wheel assembly to prevent external contaminants from entering the central cavity of the handle via the opening adjacent the control lever,
wherein the control wheel assembly includes a control wheel having an annular groove on a periphery thereof to receive a pull wire therein, and
wherein the arcuate member is further configured to overlay the annular groove to prevent the pull wire from coming out of the annular groove.

12. The endoscope device of claim 11, wherein the handle comprises a first shell and a second shell joined together to form the central cavity therein, and wherein the control wheel assembly is rotationally secured within the central cavity adjacent the opening.

13. The endoscope device of claim 11, wherein a portion of the handle proximate to the opening has a curved configuration corresponding to the control wheel assembly.

14. The endoscope device of claim 11, wherein the control wheel assembly comprises at least a first control wheel and a second control wheel rotationally coupled to the first control wheel, wherein the arcuate member is formed on at least a portion of an outer periphery of the second control wheel.

15. The endoscope device of claim 14, wherein the opening in the handle has a first length and a first width, and wherein the arcuate member has a second length and a second width, wherein the second length of the arcuate member is longer than the first length of the opening and wherein the second width of the arcuate member is wider than the first width of the opening.

16. The endoscope device of claim 15, wherein the second length of the arcuate member extends along at least half of the outer periphery of the second control wheel.

17. The endoscope device of claim 11, wherein the control wheel assembly further comprises a third control wheel rotationally coupled to the first control wheel and the second control wheel, wherein the third control wheel includes an second annular groove on a periphery thereof to receive a second pull wire therein, and wherein the arcuate member on the second control wheel is further configured to prevent the second pull wire from coming out of the second annular groove in the third control wheel.

18. The endoscope device of claim 17, wherein the second width of the arcuate member is sufficient to cover the annular groove in the first control wheel and the second annular groove in the third control wheel.

\* \* \* \* \*